United States Patent [19]
Benaron

[11] Patent Number: 6,167,297
[45] Date of Patent: Dec. 26, 2000

[54] DETECTING, LOCALIZING, AND TARGETING INTERNAL SITES IN VIVO USING OPTICAL CONTRAST AGENTS

[76] Inventor: David A. Benaron, 25 Siesta Ct., Portola Valley, Calif. 94028-7436

[21] Appl. No.: 09/305,855

[22] Filed: May 5, 1999

[51] Int. Cl.[7] ........................................................ A61B 6/00
[52] U.S. Cl. .................................................................. 600/431
[58] Field of Search ...................................... 600/431, 407, 600/411; 250/302, 303; 424/1, 1.1, 1.2, 1.21, 1.22, 1.23, 1.24, 1.25

[56] References Cited

U.S. PATENT DOCUMENTS

| | | | |
|---|---|---|---|
| 4,805,623 | 2/1989 | Jöbsis | 128/633 |
| 5,280,788 | 1/1994 | Janes et al. | 128/665 |
| 5,303,026 | 4/1994 | Strobl et al. | 356/318 |
| 5,349,954 | 9/1994 | Tiemann et al. | 128/634 |
| 5,406,950 | 4/1995 | Brandenburger et al. | 128/662.02 |
| 5,413,108 | 5/1995 | Alfano | 128/665 |
| 5,494,031 | 2/1996 | Hoeft | 128/633 |
| 5,555,885 | 9/1996 | Chance | 128/654 |
| 5,596,992 | 1/1997 | Haaland et al. | 128/664 |
| 5,601,087 | 2/1997 | Gunderson et al. | 128/664 |
| 5,647,368 | 7/1997 | Zeng et al. | 128/665 |
| 5,672,333 | 9/1997 | Rajagopalan et al. | 424/9.6 |
| 5,697,373 | 12/1997 | Richards-Kortum et al. | 128/664 |
| 5,698,397 | 12/1997 | Zarling et al. | 435/6 |
| 5,722,407 | 3/1998 | Klingenbeck-Regn et al. | 128/653.1 |
| 5,782,764 | 7/1998 | Werne | 600/411 |
| 5,782,770 | 7/1998 | Mooradian et al. | 600/476 |
| 5,800,350 | 9/1998 | Coppleson et al. | 600/372 |
| 5,840,507 | 11/1998 | Fruehauf | 435/7.23 |
| 5,851,527 | 12/1998 | Hansen | 424/178.1 |
| 5,853,370 | 12/1998 | Chance et al. | 600/473 |
| 5,857,463 | 1/1999 | Thurston et al. | 128/659 |
| 5,861,248 | 1/1999 | Russell et al. | 435/6 |
| 5,865,754 | 2/1999 | Sevick-Muraca et al. | 600/476 |
| 5,899,865 | 5/1999 | Chance | 600/473 |

FOREIGN PATENT DOCUMENTS

WO 97/36619 10/1997 WIPO.
WO 98/10698 3/1998 WIPO.
WO 98/48838 11/1998 WIPO.

OTHER PUBLICATIONS

Svanberg, K., et al., "Clinical Multi–Colour Fluorescence Imaging of Malignant Tumors—Initial Experience", *ACTA Radiologica* 39 (1998), 2–9.

Patel, Jayesh, et al., "Measurement of Cerebral Blood Flow in Newborn Infants Using Near Infrared Spectroscopy with Indocyanine Green", *Ped. Res.* vol. 43, No. 1. (1998) 34–39.

Hüber, Martina M., et al., "Fluorescently Detectable Magnetic Resonance Imaging Agents", *Am. Chem. Soc.* (1998) 242–249.

Hintz, Susan R., "Stationary Headband for Clinical Time–of–Flight Optical Imaging at the Bedside", *Photochem. Photobiol.* 68(3) (1998), 361–369.

*Primary Examiner*—Teresa Walberg
*Assistant Examiner*—Daniel Robinson
*Attorney, Agent, or Firm*—Flehr Hohbach Test Albritton & Herbert LLP

[57] ABSTRACT

A system for detecting, localizing and targeting a medical instrument toward a target tissue within the body using an optical contrast agent in which a light source (102) is optically coupled to the tissue to be diagnosed (135), a light detector (174) is optically coupled to the tissue to detect a portion of the light which passes through the tissue, and either one or both of the light source and light detector are coupled to a medical instrument (130) used in a medical procedure. A contrast locator engine (184) receives a signal from the detector and provides an target tissue output signal (195) based upon the localization and distribution of the contrast agent, allowing the target tissue to be detected, located, or imaged, and for the medical instrument to positioned or targeted relative to the target tissue, and for allowing the accuracy of placement or the progress of a procedure to be assessed in real time. A method for the system is also described.

37 Claims, 11 Drawing Sheets

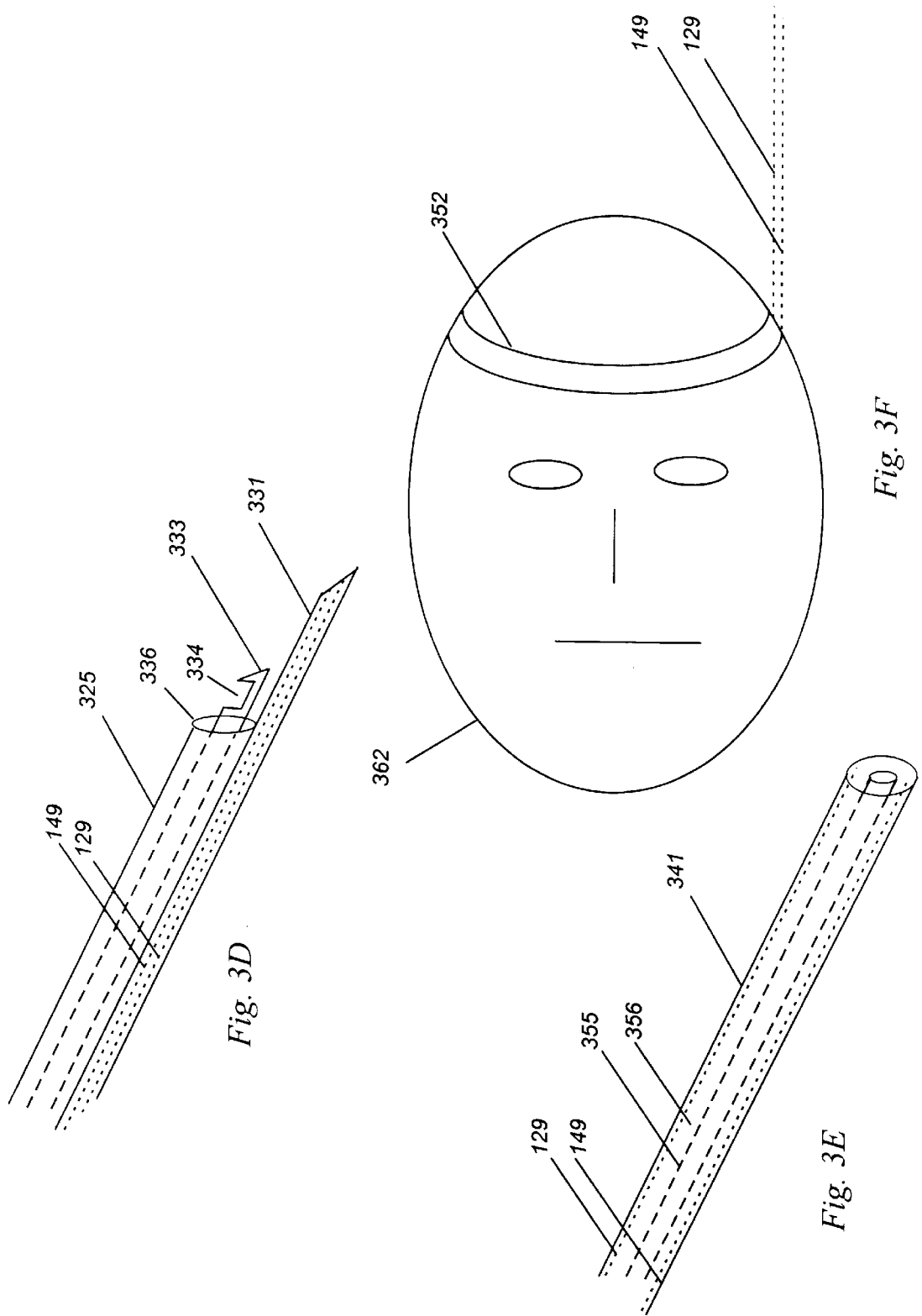

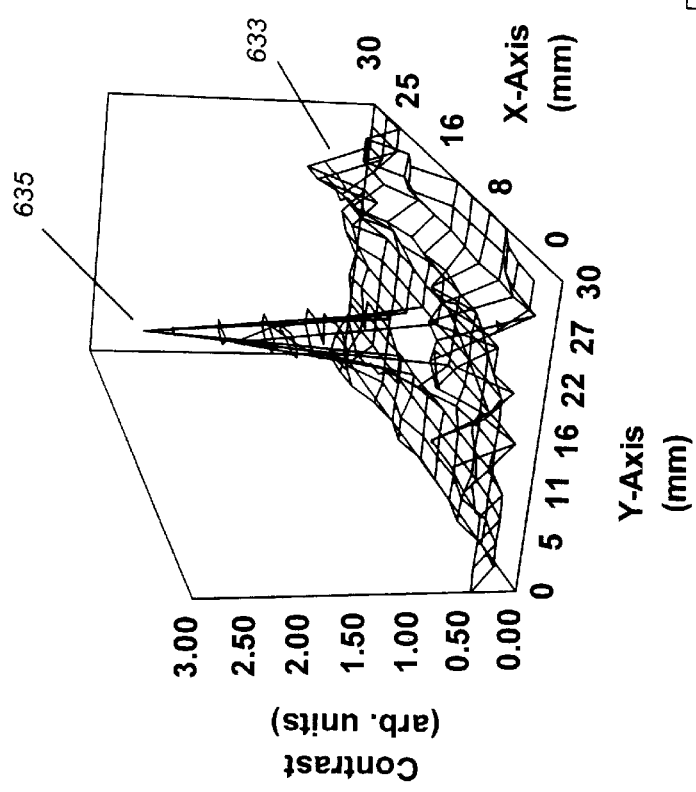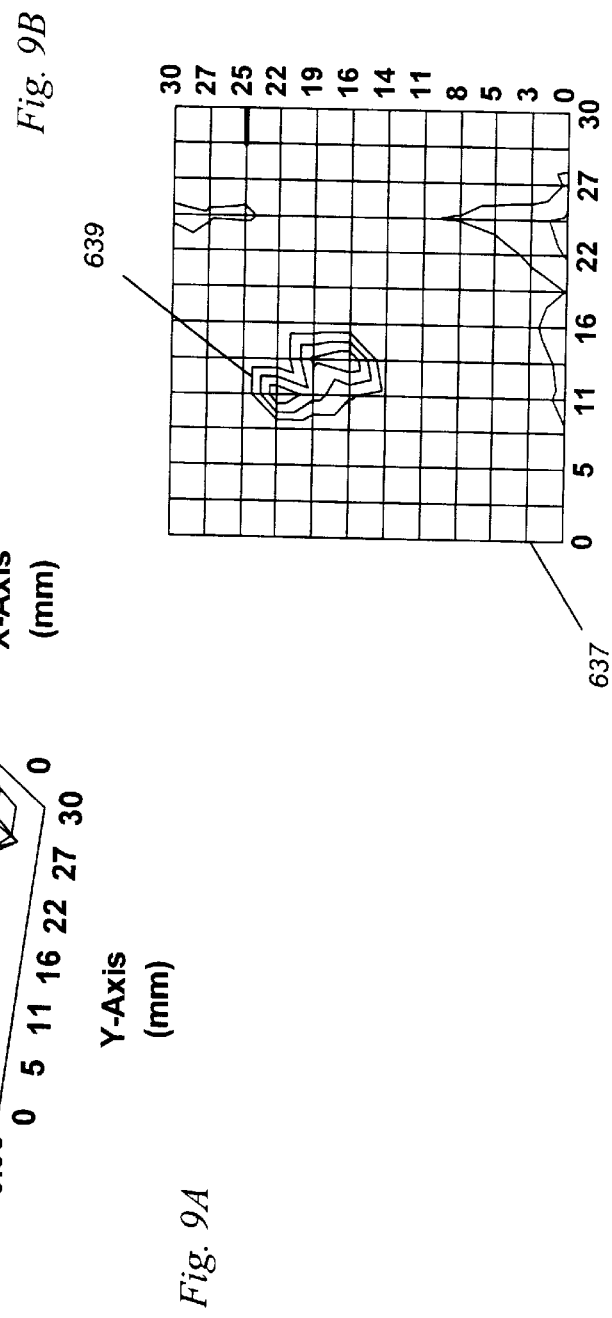
Fig. 9B
Fig. 9A

DETECTING, LOCALIZING, AND TARGETING INTERNAL SITES IN VIVO USING OPTICAL CONTRAST AGENTS

FIELD OF THE INVENTION

The present invention relates to systems and methods for using medical instruments to determine the location or distribution of an exogenous optical contrast agent in vivo, and more particularly relates to coupling use of an invasive medical instrument to use of an optical contrast agent to target the instrument to a particular site in the body.

BACKGROUND OF THE INVENTION

Identifying hidden target tissues using medical tools and guiding a medical instrument to target sites buried within the body are important medical skills. For example, detecting the presence or absence of prostate cancer with a medical probe would decrease the number of unnecessary biopsies. Similarly, using a medical instrument to detect the location of lymph nodes most likely affected by cancer prior to making a surgical incision would allow for a much smaller surgical incision and a less extensive surgical exploration. As another example, navigating a biopsy needle into a liver tumor would improve the chances that a physician will obtain an accurate biopsy specimen. Last, accurately knowing the margins of disease in a diseased organ would allow for the disease to be completely removed while sparing the maximum amount of normal tissue.

In order to achieve good detection and targeting of buried tissue, and to avoid a blind approach to a target site, many invasive procedures are attempted using medical instruments monitored or tracked using medical imaging or image guidance. A limitation of conventional imaging-based approaches is that they require an inherent, identifiable signal from the target tissue. An identifiable signal may be as simple as a different appearance on ultrasound or CT scan. However, key molecules in many disease processes may not possess strong, distinguishing features that allow them to be easily imaged. In such tissues, there may be no readily detectable difference from the surrounding tissue, and thus there will be little or no indication on a conventional image of the location of the target tissue or disease. Examples of this include the events associated with the activation of certain genes or cell surface receptors in the body, which may be important in the localization or detection of certain cancers. Prostate cancer, for example, is not well seen on CT, MRI, or ultrasound. As a result, even when prostate cancer is present at the time of biopsy, 20% of all prostate biopsies will be falsely negative for cancer. Other examples include the events associated with infection, which may be important in the selection of an appropriate antibiotic therapy. Thus, conventional imaging is limited in that it fails for many types of diagnostic and therapeutic procedures that would in theory benefit from image guidance.

Contrast agents have been used in the past for medical monitoring and imaging when the inherent or native signal in vivo is absent or poor. A contrast agent serves to provide a strong, identifiable signal to an otherwise poorly detectable tissue site. In this regard, use of contrast is known in the art, and is a routine part of conventional imaging approaches such as CT, MRI, and occasionally ultrasound.

A drawback to ultrasound contrast is that the contrast has tended to consist of physical agents, such as bubbles, which are limited in that they have not been tissue targetable and have been short lived. This makes such agents poor for real time localization and targeting. Many types of site-specific binding moieties are known, including antibodies (e.g., U.S. Pat. No. 5,851,527) and nuclear receptors (e.g., U.S. Pat. No. 5,840,507), and these can be used for targeted delivery of contrast agents. Targetable contrast has been reported for use in vitro and in vivo for MRI and nuclear medicine (e.g., U.S. Pat. No. 5,861,248). However, use of targeted MRI, nuclear medicine, and CT contrast agents is limited by their low contrast. A targeted MRI contrast agent, for example, may increase the native signal by only 20–50% over MRI background. This reduces the ability to detect small lesions, and makes real time targeting more difficult.

Another disadvantage to the use of contrast agents in CT and MRI is that most CT and MRI systems do not operate in real time (real-time MRI exists, but is awkward to use and expensive). However, patients are not static objects. Tissues move and organs shift, so that a CT or MRI image obtained even a few minutes before a procedure may no longer be accurate when needed as an image guidance reference. For example, the liver moves with breathing, and the prostate and breast move with changes in position. Thus, the location of a tumor on the CT or MRI scan with respect to a marker on the patient can change. Similarly, many CT and MRI image guided systems use images collected prior to an intervention, and do not reflect any interaction of a tool with the body. Thus, when the brain moves during neurosurgery, an image that was correct before the skull was opened may now be dangerously inaccurate. Therefore, in the absence of real-time feedback, many image guided surgery techniques that rely on static images can prove inaccurate.

Use of contrast that is optically based raises the possibility of real-time, portable guidance and monitoring. In this regard, contrast agents that have optical properties detectable in vivo are known. For example, cardiac output, liver function, lung blood flow, brain blood flow, and retinal blood flow/transparent structure have been measured or in vivo or ex vivo using optical dyes (e.g., U.S. Pat. No. 5,494,031, Patel et al. in *Ped Res* 1998;43(1):34–39). In these examples, the contrast agent is used to measure a bodily function, such as blood flow or enzymatic clearance from the bloodstream. The concentration of a drug or dye has also been measured in the bloodstream (e.g., U.S. Pat. No. 4,805,623). However, none of the preceding optical contrast methods or devices teach detection or localization of contrast distribution through opaque tissue, nor detection or localization of tissue types. Further, these systems are not coupled to medical devices or instruments used in the performance of a medical procedure, nor do they allow targeting of invasive medical instrument to specific tissue sites.

More recently, new optical dyes have been reported that may have application to real-time optical localization and targeting (e.g., U.S. Pat. No. 5,672,333, U.S. Pat. No. 5,698,397, WO 97/36619, WO 98/48838, Hüber et al. in *Bioconjugate Chem* 1998;9:242–249). These dyes are useful for microscopy or in vitro or in vivo, and some have multimodality functionality for both MRI and optical imaging. The listed patents add to the list of optical agents available for use in the body, but do not demonstrate or suggest systems for their use in medical devices or instruments for the detection or localization of target tissues, nor do they suggest or teach methods for the targeting of invasive medical instruments to specific tissue sites.

Optical methods have been developed for both external imaging and for incorporation into medical devices. Devices for imaging or measuring spectroscopic features of living tissue include U.S. Pat. No. 5,137,355, U.S. Pat. No. 5,203,339, U.S. Pat. No. 5,697,373, U.S. Pat. No. 5,722,407, U.S. Pat. No. 5,782,770, U.S. Pat. No. 5,865,754, WO 98/10698, Hintz et al. in *Photochem Photobiol* 1998;68(3):361–369, and Svanberg et al in *Acta Radiologica* 1998;39:2–9. One drawback to these systems is that they are typically large, bulky imaging systems, and some are quite expensive. Another drawback is that many of these devices are not configured for incorporation into medical tools or instruments. In fact, many teach away from coupling to a medical device or instrument, relying instead on a noncontact or noninvasive imaging system. Some of these are non-penetrating systems, such as endoscopes, or non-contact systems. Such systems are superficial imaging systems that merely image the surface of a tissue, and they do not image through opaque tissues to allow detection and targeting of deep tissues, nor is it obvious how such endoscopic or external imaging systems would readily be coupled into medical or surgical tools to penetrate through tissue to reach deep tissue sites. Another disadvantage is that many of these systems teach away from use of contrast, relying instead upon native spectroscopic signals. For those approaches that do suggest concurrent use of optical contrast agents, such as indocyanine green, coupling of these systems to medical instruments using exogenous contrast to locate or target specific tissue sites hidden through opaque tissue is neither taught nor suggested, nor is use of a contrast agent for the targeted delivery of an invasive device to a target tissue suggested or taught. In fact, these devices teach away from use in invasive tools, featuring noninvasive or endoscopic use as a strength, and none of these systems is well suited for use as an invasive device.

Invasive or contact-marking medical instruments equipped with optics, such as catheters, needles, and trocars, include U.S. Pat. No. 5,280,788, U.S. Pat. No. 5,303,026, U.S. Pat. No. 5,349,954, U.S. Pat. No. 5,413,108, U.S. Pat. No. 5,596,992, U.S. Pat. No 5,601,087, U.S. Pat. No. 5,647,368, U.S. Pat. No. 5,800,350, and others. Some of these devices are endoscopic, and do not image through opaque tissue. Others are invasive medical instruments and devices, but they do not detect or localize target tissues using exogenous contrast, nor do they allow targeting of an instrument to specific tissue sites using an in vivo contrast signal from an exogenous contrast agent. Several of these patents explicitly teach away from the use of contrast.

An alternative to the use of a contrast agent is use of an emitting reporter. In this regard, use of emitting reporters is known in the art. For example, in nuclear medicine and PET scanning, agents that spontaneously emit a particle or photon provide a signal to identify to localization of the emitter agent. Targeted instruments based upon non-optical emitters have been built (e.g., U.S. Pat. No. 5,857,463). A drawback to nearly all emitter-based systems is that they suffer from low signal, which is due to use of radioactive or ionizing emitters that produce a signal only intermittently (such as a particle decay) and at low intensity, forcing long integration times that make real time imaging and precise localization slow or difficult. This low signal presents a particular difficulty when using a moving medical instrument, or when targeting a tissue using a moving probe, both of which require a strong signal for reliable, rapidly updated real time analysis.

An optical equivalent to the external imaging of emitter reporters is use of light-emitting beacons that spontaneously generate light, such as the luciferase protein family. Such approaches are not contrast agents in the sense of this invention, as optical contrast agents modify the incident radiation rather than spontaneously generate light as is done using emitting optical reporters. An additional drawback for optical emitting reporters, beyond those shared by all emitting reports, is that they require a nearly light-free environment, making use real-time in vivo in humans difficult. Of note, such optical emitting reporters have not been coupled to a medical devices, such as an invasive targeted therapeutic device.

None of the above systems, agents, or methods suggest how to combine an optical contrast agent and a medical tool or instrument into a coherent system for tissue localization and targeting, nor how to perform optical contrast-guided surgery, nor how to target invasive instruments toward tissue using the tracking signal of an optical contrast agent, nor how to identify target tissues using a medical tool based upon the localization and distribution of an optical contrast agent. A real-time optical system and method to guide devices to target tissue sites, or to detect, localize, and image tissue targets using a contrast-influenced signal passing through opaque tissue to a medical tool, has not been taught, nor has such a tool been successfully commercialized.

SUMMARY AND OBJECTS OF THE INVENTION

The present invention relies upon the optical characteristics of tissue in the presence of an internalized exogenous contrast agent to allow for a rapid imaging, localization, positioning, and targeting of tissue in vivo.

A salient feature of the present invention is that an exogenous optical contrast agent can be administered to a subject, either in an active form or as a pre-active prodrug, and that optical elements can be integrated into medical instruments used internally for real-time feedback during targeted interventions performed using the instrument. Alternatively, the optical sensors can be integrated into medical instruments used externally for detection of the distribution or localization of at least one form of contrast agent or of specific tissue types. Accordingly, an object of the present invention is to provide a system and method to detect, localize, image, and target tissue using an exogenous optical contrast agent administered to the subject followed by optical detection.

A second object is that this detection, localization, imaging, and targeting can be made using one or more optical elements embedded, at least in part, within the medical instrument being guided, positioned, or targeted. This can be achieved in a way that minimally alters the look and feel of the medical instrument, if desired.

A third object is that a determination of the accuracy of placement of a medical instrument can be made by measuring a characteristic of the optical contrast agent within the tissue after administration to a subject, whether to yield a numeric accuracy value, a correct vs. incorrect discrimination, or other accuracy determinations, and that such placement determinations can be used to determine probe position.

A fourth object is that localization of an invasive medical instrument with respect to a target tissue can be made. This localization can be in the form of a determination of the distance or direction of the device to the target tissue, or the device can be localized in space in one or more dimensions. Such information can be used to make a guidance signal for the purpose of guiding the medical instrument to a target location. Alternatively, the localization can be in the form of a determination of the tissue compartment in which the device is currently placed, such as tumor, prostatic capsule, skin, muscle, or blood vessel.

Another object is that an invasive medical instrument can be monitored during placement in real-time. This allows coupling with other approaches, such as conventional image-guided surgery, while allowing for small course corrections. This reduces errors that arise when a previously-collected image is used for image-guided surgery, without reflecting changes in the tissue that have occurred over time, such as changes in position, or that occur as a result of use or placement of the invasive instrument.

Another object is that an invasive medical instrument can provide feedback during an invasive procedure. For example, a tool can be used to nibble out a tumor from the inside, and the process can be continued until no further contrast remains, signifying that the tumor has been effectively removed and the surgical margins are clean. Similarly, an interlock can be provided such that the tool nibbles until a particular area is clean of contrast, but then allows other areas to be nibbled, resulting in that only the tumor is removed from the tumor site. Last, the feedback can be used to control any process of cell destruction, such as an ablation process, using the contrast feedback from the targeted tissue.

Another object is that any medical probe or instrument can be modified to perform this guidance or targeting function, such that measurements may be made using existing medical equipment, modified to hold either emitter elements, detector elements, or both. Such modified instruments include modified needles, probes, scissors, catheters, scalpels, trocars, tips of surgical tools, or other devices. The ability to guide, locate, and target using contrast can also be designed into new or unforeseen medical probes or devices. This function can be incorporated into replaceable device tips.

Another object is that the localization can be enhanced by concurrent or a priori knowledge, such as the known optical spectral characteristics of target tissues or tissues expected to be encountered during placement (which can be stored for reference in the device or in the probe), the area of the body the physician is working (such that far away tissues need not be considered in the analysis), or information from other medical scans (such as a CT or MRI scan). This contrast approach may be combined with other real-time approaches, such as a combination of an ultrasound probe and an optical instrument to produce an overlay of an optical contrast image upon a standard ultrasound image. Such a combination would provide both structural (ultrasound) and biochemical (optical) images simultaneously.

Another object is that this data can be enhanced by collection over time. In many medical applications, the value of a measurement is enhanced by determination of temporal characteristics. For example, the rate of accumulation of contrast over time, or changes with an intervention, may help discriminate one tissue from another. Subtraction of the data at one point in time from data collected at a second point in time can yield improved data.

Another object is that this guidance, localization, or accuracy of position represents a decision point upon which a human response may be initiated, such as with a visual guidance display or an alarm bell that signals correct placement, or an interlock decision may be initiated, such as via an output signal attached to a medical device.

A final object is that the detection, localization, or imaging information can be presented to the user in a number of ways, such as a visual left/right guidance signal, a visual image processed from ease of interpretation, a displayed word describing placement, a variable alarm to indicate an increasing accuracy of placement by changes in pitch or speed or intensity of the tones, or other manners of presentation, in such a manner as to allow the user to gain an incremental understanding of the placement of the probe, or accuracy of placement.

The systems and methods as described have several advantages. One advantage of optical contrast is that optical contrast agents can achieve their contrast in a number of ways. The interaction with the illuminating light can include absorbance, polarization, optical rotation, scattering, fluorescence, Raman effects, phosphorescence, or fluorescence decay, and measures of a contrast effect may reasonably include one or more of these effects. Examples of optical contrast agents includes isosulfan blue or other absorbing contrast agents, indocyanine green, porphyrins, or other fluorophores, methyl red (a pH-responsive dye) or other biologically responsive dyes, colored or fluorescent proteins and other gene products, quantum dots and other spectroscopically distinct physical constructs, and contrast-filled micelles. Methods of detecting the contrast may include measurement of diffuse light, gated time resolved or frequency-resolved methods, hyperspectral detection or imaging, and the like.

Another advantage is that administration of the an optical contrast agent can be performed in a number of ways. Contrast agents can be injected, ingested, or even synthesized within the subject using genetic mechanisms or encapsulated biofactories. In the genetic example, contrast can be delivered as a gene, and the gene product synthesized within the subject is a protein or product that interacts with illuminating light field. Further, as methods are known for the delivery of the contents of a viral particle into a living mammalian cell, contrast agents, or the genes encoding for a contrast agent, can be delivered to a subject by means of a virus that "infects" tissues with a contrast agent. This virally-delivered contrast agent can be a prodrug that requires activation, and is activated when placed into a cell containing certain proteins or ribonucleic acid sequences. The allows for the production of contrast in cells expressing certain internal genetic traits, such as prostate specific antigen (PSA) or prostate specific membrane antigen (PSMA) over-expression in prostate cancer cells, even if no identifying cell surface receptors exist on the target tissue. Even proteins used in the luciferase emitter reporter system can be made to reactively emit light as a contrast agent when illuminated. As a second example, contrast can be sprayed or delivered from the tip of the invasive instrument, and used to bathe or infuse the tissue nearby the instrument tip. The signal from this contrast can then be monitored locally to define tissue margins or detect the presence of certain tissue types, such as tumors. Such an approach can be particularly powerful as a way to guide a tool to remove tissue, and the tissue can be considered removed when local infusion of the contrast agent no longer produces a tissue optical signal.

Another advantage of optical contrast is that the contrast agent itself can be quite small, allowing delivery to and targeting of specific tissue sites, including nearly any tissue or cell region. The contrast agent may be achieve its localization by chemical or physical means, and such targeting methods are well known to those skilled in the art. For example, the contrast may distribute on the basis of solubility, diffusibility, transport protein affinity, or the contrast may be bound, ionically or covalently, to a localizing moiety such as an antibody, antibody fragment, receptor or translocator binding site or substance. Alternatively, the contrast agent may be bound or encapsulated, such as in a microbubble or liposomal structure, and the surrounding structure may then be targeted using surface structures. Targetable sites are known for prostate cancer, breast cancer, and other diseased sites. In the breast, targetable binding sites fall into two groups. The first are those antigens and receptors expressed or over-expressed in cancer as compared to normal tissue. Exemplary sites in this class include CEA, MUC1 and other mucins, mammaglobin, HER-2/neu, EGF-R, ER, PR, and others. Some of these are internalizing receptors, allowing intracellular delivery of the agent. Targeting of this group of sites produces a contrast agent with specificity for one or more subclasses of cancer. A second group of potential targets for labeling are those antigens present on all cells of a class (such as breast epithelial cells). Use of receptors present on normal tissue allows for detection of that tissue outside of the primary site (the primary site will label strongly as well, preventing detection of cancer within the parent tissue). In the prostate, an exemplary targeting site is PSMA; in colorectal cancer, an exemplary targeting site is radiolabeled anti-CEA antibody fragment. In addition, internal, targetable binding sequences are known to exist in the body for certain cancers, and for other diseases as well.

Another advantage to use of optical contrast is that the signal can be very bright when compared with contrast agents for MRI, CT, or compared to emitters for PET and nuclear medicine. The local fluorescence contrast from a targeted fluorescence contrast agent may be 1,000,000 times greater than the contrast signal achievable from a similarly targeted radioemitter. This allows greater signal production while using relatively smaller doses of contrast agent.

Another advantage of optical contrast is that multiple contrast agents, each of distinguishable optical signature in vivo, can be added to provide the power of simultaneous, multiple labeling for different affinities and receptors. A target cancer may be a cell that expresses two or more receptor sites, and double, triple, or multiple contrast agent labeling is achievable using optical contrast agents with unique, differentiable optical characteristics.

Another advantage of optical contrast agents is that the contrast agent may be administered in a pre-active form, and the production of contrast is then achieved by a bioactivation step in which the contrast agent requires activation through a biological interaction before producing or reducing its native signal. Such interactions include enzymatic processing, conformational changes, receptor binding, gene expression, and the like. For example, a conformational change can be the result of a pH change or of a binding event that swings fluorescence quenching groups into or out of position, decreasing or increasing the signal in response to binding. Similarly, an enzymatic processing may be an irreversible cleavage that removes fluorescence quenching moieties from the contrast agent, turning on a strong signal. Last, a bioinactivation step can be used to shut off the contrast in response to a biological event.

Another advantage of optical contrast is that the contrast agent may have contrast function for other imaging modalities, such as MRI, CT, and others. This allows monitoring by more than one modality at a time.

There is provided a system for determining a measure of the location or distribution of an optical contrast agent within an opaque, radiation-scattering medium by coupling a medical instrument, used externally or invasively, with use of a contrast agent. In one example, this system has a light and light detector optically coupled to the tissue through an invasive medical instrument to detect a portion of the light which has passed through the tissue and interacted with a contrast agent in vivo. A contrast localizer receives a signal from the detector and provides an contrast localization signal, used to target a medical instrument to a particular site in the body, determine the accuracy of placement of that instrument, or provide a feedback signal to the user regarding device location and accuracy of placement. A method of targeting a probe in tissue is also described.

The breadth of uses and advantages of the present invention are best understood by example, and by a detailed explanation of the workings of a constructed apparatus, now in operation and tested in model systems, animals, and humans. These and other advantages of the invention will become apparent when viewed in light of accompanying drawings, examples, and detailed description.

BRIEF DESCRIPTION OF THE DRAWINGS

The following drawings are provided:

FIGS. 3A–3F are examples of medical instruments which can be used in the system shown in FIG. 1.

FIGS. 9A and 9B show a 2-D localization in vivo of the distribution of in human tissue containing a region with isosulfan blue contrast.

DEFINITIONS

Figure 1:
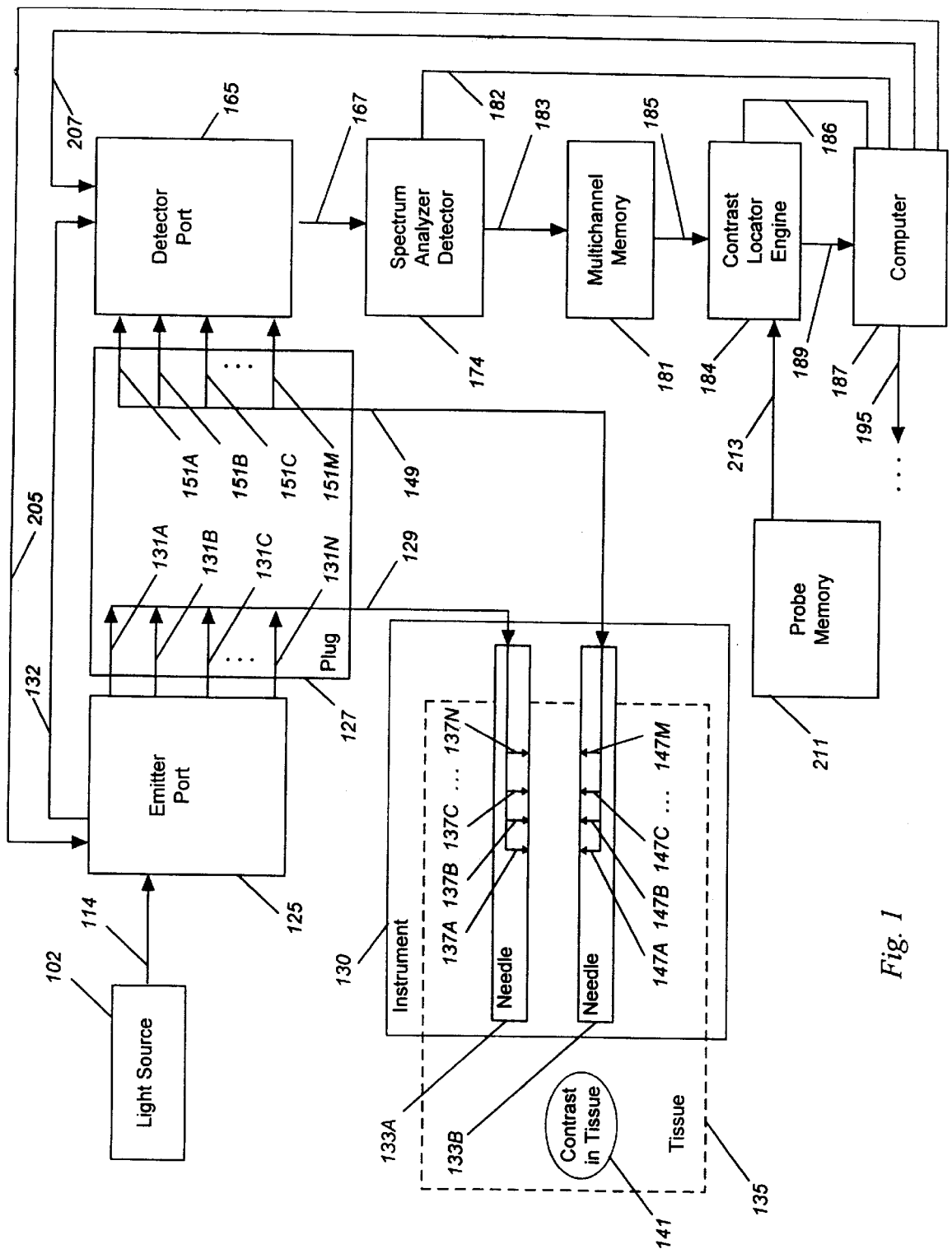
FIG. 1 is a schematic diagram of a system coupling a medical instrument to use of a targeted contrast agent in accordance with the invention.

For the purposes of this invention, the following definitions are provided:

Optical Contrast Agent: A moiety that interacts with and modifies optical illuminating radiation. Ideally, the contrast agent provides a differential contrast for the target tissue site versus other tissues. The agent may require bioactivation or bioinactivation in order to achieve this differential contrast.

Optical Emitting Reporter: An agent that spontaneously emits light without external energy sources, for example a bioluminescent protein such as luciferase when coupled to the proper substrates. An example of non-optical emitting reporters are nuclear medicine radioemitters.

Target Tissue: A tissue site for diagnosis or treatment. For prostate, a target tissue may be prostate cancer.

Tissue-Guided Intervention: The term tissue-guided intervention is used in contrast to image-guided surgery. In image-guided surgery, the location of a medical instrument is determined in space, and displayed with respect to a standard medical image, such as a CT scan or MRI scan. In this way, the surgeon can guide the surgery using the CT or MRI image as a road map, and see the medical instruments displayed on the image. In contrast, during tissue-guided intervention, the tissue at the tip of the probe is monitored, and the surgery is guided by the analysis of the tissue in contact with, or near, the tip of the medical instrument. In the present invention, the tissue guidance signal is provided by the presence of a contrast agent. Tissue guidance and image guidance can be provided simultaneously in the same patient.

Targeting: Targeting indicates that there is a target site or target tissue relative to which a needle, probe, or other medical instrument is to be placed. For example, a sentinel node in breast cancer may be targeted, such that the node can be collected for pathological examination. Included in this process measure is that a signal can be generated that reflects the accuracy of placement ("e.g., is this needle at the sentinel node yet?").

Localization: Localization is used to mean to obtain a measure of where the instrument is now. This implies an processing of the raw information contained in the detected signal into a measure of instrument location, ranging from the simple numeric distance ("how far is the target tissue from my needle?") to the very complex (e.g., "what tissues am I in or near?").

Guidance: Guidance is used to mean that a signal is generated which is indicative of the direction, depth, or distance needed for the probe to be moved to achieve a desired goal. For example, a prostate cancer biopsy needle is guided if a signal indicating left, right, deeper, straight ahead, or pull-out is generated. Such signals are guidance signals.

Accuracy of Placement: Accuracy of placement reflects a measure as to the placement of a device as compared to a target location.

Medical Device or Instrument: A tool used during the performance of a medical procedure. An invasive instrument is placed into the body, for example by puncturing the skin and penetrating the tissue beneath. An example of an invasive instrument is a biopsy needle that penetrates through the abdominal wall to collect a portion of the pancreas for biopsy.

Light: Electromagnetic radiation from ultraviolet to infrared, namely with wavelengths between 10 nm and 100 microns, but especially those wavelengths between 200 nm and 2 microns.

Opaque Tissue: Tissue is living tissue or tissue-like radiation-scattering media, such as skin, brain, bone, or even cloudy water. Opaque tissue is tissue through which light is scattered as well as absorbed. Opaque tissue is not transparent or translucent, save when viewing very thin slices removed from the body.

Body: A living animal body, including other mammals, but especially humans.

Light Emitter or Light Source: A source of light. It may be composed of a simple light bulb, a laser, a flash lamp, or another light source or combination of sources, or it may be a complex form including a light source, a transmission element such as an optical fiber, a guidance element such as a reflective prism, and other elements intended to enhance the optical coupling of the light from the emitter to the skin or tissue under study. The light source may be continuous, pulsed, or even analyzed as time-, frequency-, or spatially-resolved. The emitter may consist of a single or multiple light emitting elements.

Light Detector or Light Collector: A collector or light that generates a signal in response to the collected light. As above, it may be single or multiple, simple or complex. The detection may be performed in reflectance or in transmission. The collected light may be light that has been influenced by transmission, absorbance, scattering, fluorescence, phosphorescence, or other optical interactions of the contrast moiety with the illuminating radiation. Detection may include time-, frequency, or spatially-resolved measures.

Optical Element: A light source or light collector, or a portion of the hardware used therein.

Optical Coupling The arrangement of a light emitter (or light detector) in such a way that light from the emitter (or detector) is transmitted to (or detected from) tissue after passage through the tissue and after possible interaction with a contrast agent. This may include the use of optical elements such as lenses, collimators, concentrators, collectors, optical fibers, prisms, filters, mirrors, or mirrored surfaces. Optical fibers have two ends, which are generally interchangeable, and are referred here as the entrance end if the light is generally entering the fiber, and as the exit end if the light is generally leaving the fiber.

DESCRIPTION OF A PREFERRED EMBODIMENT

One embodiment of the system and method will now be described. The device has been tested in vivo and in vitro, including in the three examples that follow the initial description of one embodiment of the system.

In the device shown in FIG. 1, light is emitted by light source 102 (Miniature Halogen L6412, Gilway Technical Lamp, Woburn, Mass.), and travels down optical fiber 114 (200 $\mu$m core glass fiber with cladding and buffer, Spectran Specialty Optics Company, Avon, Conn.) to emitter port 125. Attached to port 125 is plug 127 which directs light to illumination fiber 129 (200 $\mu$m core, as above) and connects to instrument 130. In this example, source 102 is a broadband white light emitter. Alternatively, source 102 may be monochromatic, such as a surface mount LED or an emitter/filter combination, and could be placed directly on the probe and electronically switched rather than connected via fiber optics. Illumination fiber 129 may be composed of multiple fiber elements, 131A through 131N, to allow illumination of multiple illumination sites, perhaps illuminated at different sites at different times or at different wavelengths. Optional reference fiber 132, bypasses the tissue or sample for use in monitoring the optical characteristics of source 102.

Illumination fiber 129 connects to instrument 130 and passes into needle 133A that has been placed with the tip in tissue 135. Light from fiber 129 passes through needle exit port 137A and into tissue 135, and a portion of this light potentially encounters contrast-stained tissue 141. Light traveling through tissue 135 is collected at returning to needle collection port 147A by collection fiber 149 passing from needle 133B to plug 127. In turn, plug 127 connects to detector port 165. Alternatively, if multiple emitter fibers are present, then there are N emitter ports 137A through 137N. Similarly, if multiple detector fibers exist, then there are M detector ports 147A through 147M, connecting via multiple fiber elements 151A through 151M in collection fiber 149. Also, there may be more than one needle or probe, such as in optical forceps, in which the emitting fibers and the collecting fibers may be in different needles or probes (not shown). Of note, needle 133A and needle 133B can be separate needles. In this example, however, they are assumed to be parts of the same needle 133A/133B and are treated as a single unit.

Light from collection fiber 149, or from reference loop fiber 132, is chosen for monitoring by detector port 165, and sent via output fiber 167 to optical analyzer 174 (Ocean Optics Spectrophotometer, Model SD2000, Dunedin, Fla., or equivalent), which records the light, and transmits an electronic signal to be stored in multichannel memory 181(A/D-converter board Model PCM-DAS16/330-1, Computer Boards Inc., Mansfield, Mass.) via cable 183. Multiple spectra can be stored in memory 181, allowing for collection of standardization spectra for correction of the spectra for instrument response, and also allowing for multiple regions of the tissue to be sampled and later compared. Spectra stored in memory 181 are then used to determine the location of the needle by contrast locator engine 184.

Contrast engine 184 is now described. Contrast engine 184 is a computer configured so as to perform identification of the optical signature of contrast agent 141. In this example, computer 187 that runs spectrum analyzer 174 via cable 182 also runs contrast engine 184 via cable 186, and this function is performed adequately by a laptop computer (AMS Laptop Pentium™ 120 MHz computer, Model AMS SY19-T40177 Travel Pro 1900, available through Ocean Optics, Dunedin, Fla). Contrast engine 184 performs a single value decomposition of the first differential of the reference spectra, in order to identify the effective contributions of the contrast agent to the resultant spectra over a selected set of wavelengths, after transmission over cable 185. Optionally, engine 184 may use the characteristic spectroscopic signals from the component tissues near the needle to identify these tissues by type, and methods of doing this are known in the art. The result of this contrast analysis is passed to computer 187, which collects and processes the determined the contribution of the contrast agent, as well as any identified tissue types, via cable 189.

Processing of the determined localization or distribution of the contrast agent, or of any targeting of instrument 130 by computer 187 may consist of the computation of a graph or image, or the calculation of a number, such as a distance. The result of this calculation, which is a measure of the distribution and localization of contrast agent 141 based upon the detected signal, is output 195. Further, emitter port 125 and detector port 165 may be under the control of computer 187 via cables 205 and 207, respectively, to allow for control of the data collection and for switching between fiber elements in multifiber cables, such as 131A through 131N or 151A through 151M. Computer 187 may be a different computer than that used in locator 184, or the same computer may be used for both functions. Note that optional reference fiber 132 allows calibration of light source 102, and that such calibration information may be stored in memory 181.

Output 195 is now more fully discussed. The output is a preprocessed signal that allows the user to obtain information regarding the distribution and localization of contrast agent 141, of the location of the probe with respect to a target tissue, either in absolute terms (e.g., accurately placed or not) or in relative terms (distance and angle from tissue to be biopsied).

Alternatively, or in addition, a reference database may be stored as an internal database within memory 181 or contained within programmable probe memory 211 and transmitted to locator 184 via probe cable 213 for use in locating the probe and determining and/or accuracy of placement. The reference database may contain various information needed to make location decisions, such as key features used to discriminate contrast 141 from other signals, or optionally including a library of characteristic discriminant features from previously identified tissues. Information in this database may then be used by locator 184 in making targeting decisions using standard methods (least squares fits, partial components regression, neural networks, etc.).

Last, multiple contrast agents may be used, such as in double or triple labeling studies. In such cases, the target may be tissue which displays more than one targeted feature. Contrast engine 184 may be configured so as to be able to detect more than one contrast agent in use at a given time.

Figure 2:
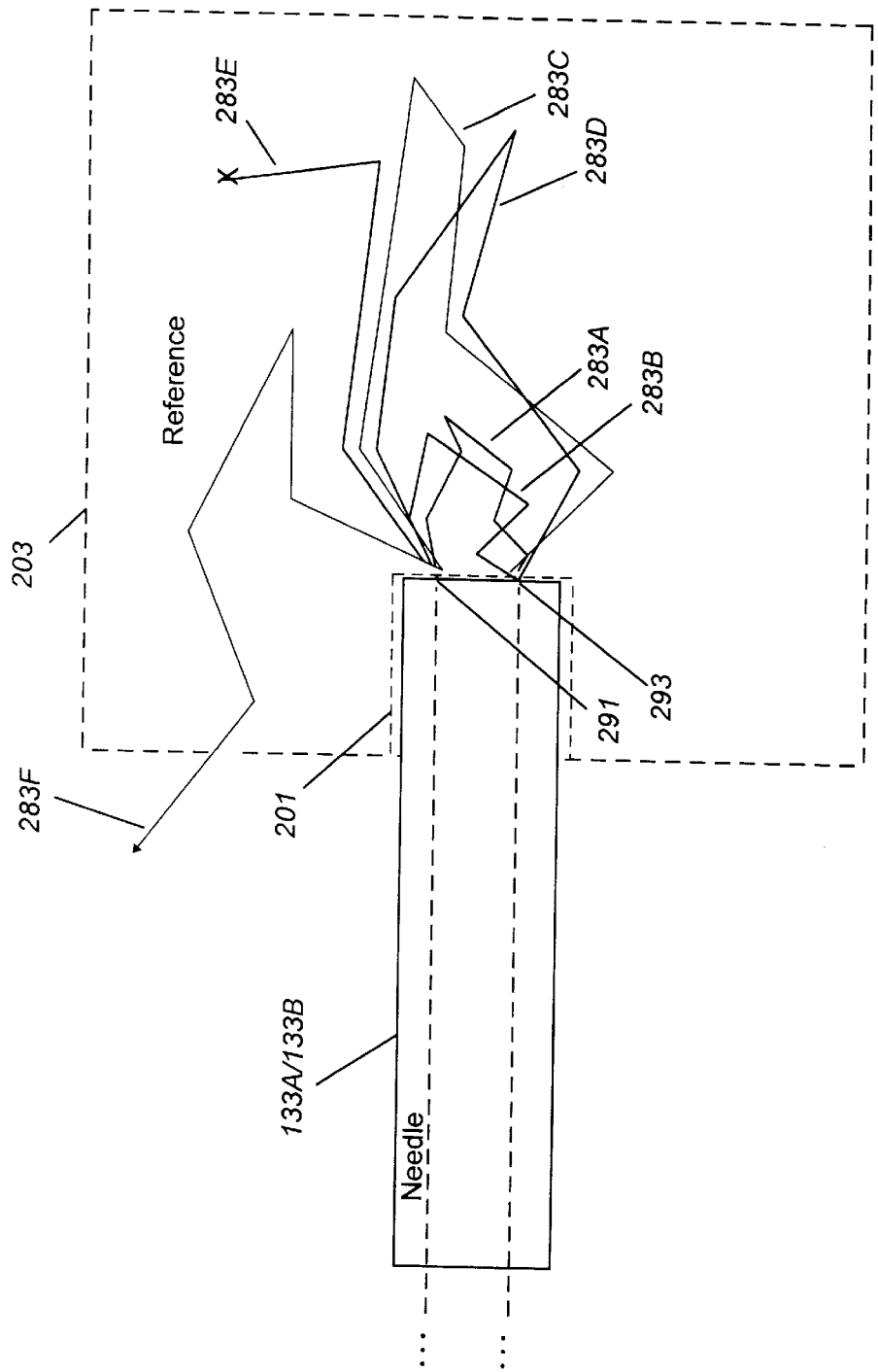
FIG. 2 demonstrates light scattering through a reference plastic and illustrates that light diffuses through the measured medium.

Operation of the device is now described. First, the instrument response is determined, in order to produce an instrument response baseline. Upon first use, tip of needle 133A/133B of instrument 130 is located into hole 201 in scattering plastic reference 203, as shown in FIG. 2. Reference 203 scatters light, but does not absorb light significantly. Referring back to FIG. 1, light from source 102 illuminates fiber 129, while detector port 165 collects light from collection fiber 149. Such spectra, collected between the two needle ports and through an opaque scattering sample using particular emitter-detector fiber pair, are called sample illumination spectra. Detector port 165 then collects light from reference fiber 132. Such spectra, collected from the light source without intervening tissue, are called source illumination spectra. Last, emitter port 125 is switched such that it does not transmit source light, effectively turning off the light source, and the measurements from fiber pair 129 and 149, and the measurements across fiber 132, are repeated. These non-illuminated spectra represent the background detector signal in the absence of illuminating light, and are called sample and source background spectra, respectively.

Reference 203 may be a plastic of known optical properties, or may be a resin, Silastic, or other polymer with known added absorbers and scatterers. Alternatively, reference 203 may be a liquid, such that needle 133A/133B is placed into a sterile vial of a calibration fluid during the referencing process.

Using well-known methods, the sample and source background spectra are subtracted from the sample and source illumination spectra, respectively, thus removing the background light counts and producing background-corrected spectra. Next, each intensity point in the background-corrected source spectra are divided by the corresponding intensity point in the background-corrected sample spectra, to produce a series of raw sample spectra. In this case, in which the sample is reference 203, a white-appearing material scattering fluid without significant absorption of light, the raw sample spectra represent the instrument response, and correspond to the spectra seen by the each emitter-detector pair in the probe in the absence of any real absorbance features. Alternatively, a scattering fluid such as intralipid may be used. These instrument response spectra are saved in memory 181. All future spectra in this experiment will now automatically be divided by the corresponding instrument response spectrum to produce a set of final sample spectra corrected for instrument response. If the light source is stable, a reference spectrum may not need to be collected, and a unit array, consisting of ones, can be used in place of the reference spectrum in these calculations. If a CCD or multiple detection fibers are used, there may be multiple detector elements 151A to 151M; similarly multiple emitter elements 131A to 131N may be used. In this case, after all reference measurements have been completed from emitter fiber 131A, this process is then repeated for each pair of selected emitter element 131A to 131N and detector element 151A to 151M.

Various reference spectra can also be loaded from memory, such as sample and source background spectra, if this results in a needed increase in speed.

To test the instrument response calibration performed above, reference 203 is now remeasured using the same steps listed above, to produce a second set of raw sample spectra. Next, each intensity point in these second raw sample spectra are divided by the corresponding intensity points in the saved instrument response spectra, to produce a set of final sample spectra. In this case, the raw sample spectra set and the instrument response spectra set should be similar, and thus the division of one by the other should produce an intensity of one, or nearly one, in all channels measured. Each final sample spectrum, therefore, should be flat, with an absorbance, A, defined as $A=\log_{10}=$(instrument response intensity)/(sample residual intensity) equal to zero, or nearly zero, at all points. Other types of spectra analysis, including differential spectra, normalization, and other corrections can be made within the spirit of this invention.

Once the device is corrected for instrument response, a sample tissue can be measured. In this embodiment, penetrating needle 133A/133B is used to target a medical device to a target tissue. In an alternative embodiment, emitter fiber 129 and detector fiber 149 may be embedded into a probe that can be scanned along the surface of the skin, or placed within surgical wounds. In the case of use on the skin, an image is obtained of the target tissue without penetration.

This example illustrates use of an absorbing contrast agent. However, other features can be used to derive the location of the contrast labeled tissue 141. For example, emitter 137A could emit at one wavelength, while analyzer 174 may be configured to be sensitive to fluorescent light. Techniques are known for such detection, and include time-resolved, frequency-domain, fluorescence lifetime, and other measures. Provided such measures are coupled for use through opaque or scattering tissues, and are coupled to the use of medical instruments, such alternative measures are within the spirit of the present invention.

To test the sample, penetrating needle 133A/133B is placed into tissue 135, as described earlier, and pairs of fibers, in this example fibers 129 and 149 are scanned, though other scanning arrangements may be desirable for other applications. For each fiber pair scanned, a source spectrum is also collected through reference fiber 132 to correct for changes in source intensity and spectrum, and then each sample spectrum is corrected for instrument response as described above, to generate a series of final sample tissue spectra. The result is a spectrum, or a set of spectra at different depths or locations in the tissue if more than one scan is collected or if multiple pairs are scanned, and are stored in memory 181.

Next, each corrected spectrum is passed to contrast engine 184, where it is analyzed for a measure of the distribution and localization of contrast agent 141. The result of this analysis is passed to computer 187, producing output 195 as a result. This result may be a diagnostic classification (such as the presence or absence of a specific tissue type as shown in Example 1), a table (such concentration of more than one label type as shown in Example 3), a graph (such as the presence or absence of a tissue type over time or distance as shown in Example 1), a number (such as the distance to a target tissue or a contrast signal strength as shown in Example 2), or an image (such as the location of a sentinel node as shown in Examples 2).

A discussion of the contrast locator engine now follows. In this preferred embodiment, determination of the localization and distribution of contrast agent 141 by locator 184 is performed by a computer, constructed with analysis routines, and arranged so as to provide a measure of the localization and distribution of contrast agent 141. However, locator 184 tissue classifier can be a calculator or other device configured so as to provide tissue or contrast location output. As noted above, computer 187 may be a different computer than that used in locator 184, or the same computer may be used for both functions.

Analysis methods used by the contrast locator may involve spectral features, such as peak wavelength, slope of a spectral region, or the first, second, or higher order differentials of the spectrum. Such methods of analyzing spectra are known, and methods exist for removing background signal or scattering effect, or in emphasizing low-concentration contrast concentrations. Methods of analysis include principal components and Partial Least Squares (e.g., Pirouette, Infometrix, Seattle, Wash.), least squares multivariate fits (SigmaPlot, Jandel Scientific, San Rafael, Calif.), neural networks (e.g., BrainMaker, California Scientific Software, Nevada City, Calif.), and the like, all of which are well known to those skilled in the art. For example, one method of such location would be to use a neural network. In this method, the network is "trained" using a series of contrast spectra in vivo from known tissues, and then the network is "queried" by giving the network the unknown spectrum and asking the network to yield a signal consistent with probe location, contrast location, or accuracy of targeting within the tissue. Such methods of mathematical analysis are known, and many different locating and targeting methods can be developed by those skilled in the art within the scope of the present invention. Optical path effects can also be measured, such as mean photon distance traveled, or the like, as taught in time-resolved or frequency-resolved methods. Contrast localization may be improved by using a computational comparison to set of reference criteria (spectra or features of the spectra such as the first differential of the spectrum, and threshold values upon which to make classification decisions), rather than a simple ratio, in order to arrive at a determination. Such reference values may be updated over time as better understanding of the meaning of the spectra is reached, and may even be built into the sensor itself, such that each sensor comes calibrated for a certain tissue set or for a certain diagnostic procedure. Similarly, identification could be improved by background correction and correction for the instrument response function, as is well known in the art. The known approaches for spectral analysis fall within the scope of the present invention whenever they are used to determine a measure of the location and distribution of a contrast agent, particularly when used to determine the location of a medical instrument with respect to a target tissue within a scattering medium such as human tissue. Such targeting and localization may also include methods to allow for a chemical, physical, or receptor based analysis of the tissue, allowing resolution of the optical data into concentrations of hemoglobin, water, fat, etc. Such identifications may be used to identify tissues in the body, such as cancer, nerve, artery, vein, lymph node, and muscle.

Figure 3C:
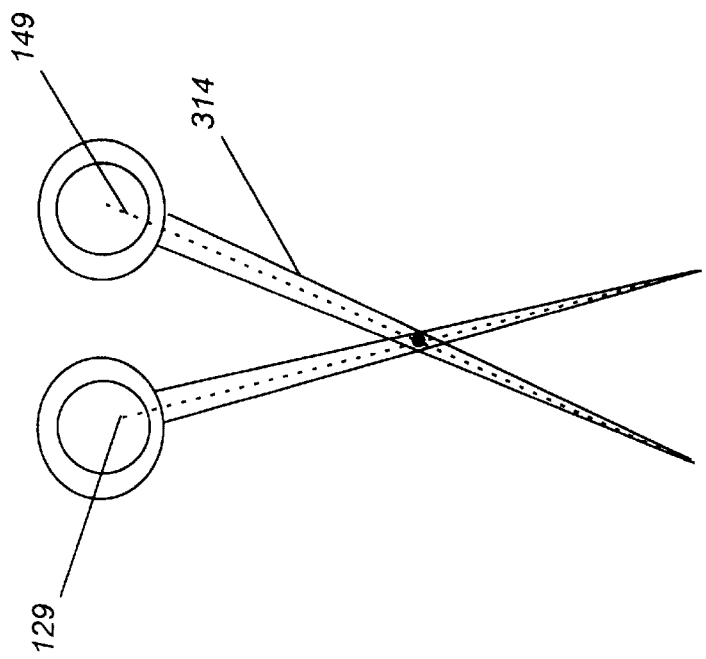
Figure 3A:
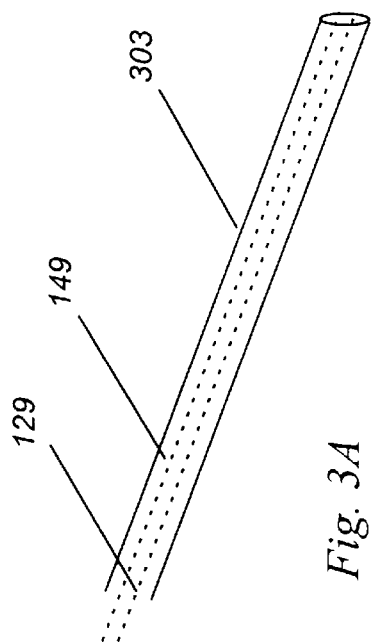
Figure 3B:
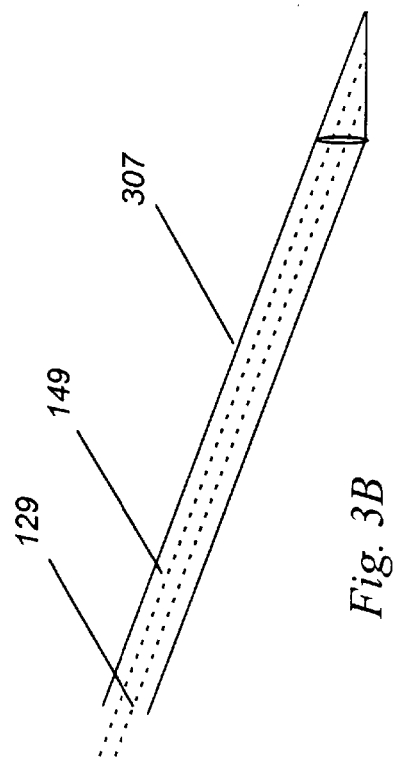

The configuration of the probe and probe construction are important. For example, it may be essential to have the fibers stabilized with respect to the tissue, to assist in the measurement. Some examples are shown in FIGS. 3A though 3F. Emitter bundle 129 and detector bundle 149, containing fibers 131A to 131N, and 151A to 151M, respectively, can be held in place by incorporation into the body of medical probe 303 (FIG. 3A), into surgical tools such as knife 307 (FIG. 3B) or into grasper 314 or scissors (FIG. 3C), or into another structure which holds the fibers in a desired optical contact with the tissue to be measured. Probe 303 may be useful externally as a surface probe. For example, prior to lymph node resection, a contrast localizing scan may assist in identifying where the initial incision should be made, resulting in a smaller scar and less morbidity.

An optical probe may also be designed to act upon the tissue in a defined way, such as biopsy probe 325 (FIG. 3D) that monitors tissue until it reaches the correct location for biopsy or nibbler 341 (FIG. 3E). Biopsy probe 325 has forward-looking, thin optical antenna 331 which is used to optically probe tissue ahead of the biopsy instrument. When it is determined that a tissue is to be collected, a biopsy specimen is taken. Instruments for collecting biopsy are known. In this example, indented trocar 333 is advanced such that tissue identified by optical antenna 331 now rests in indentation 334. Cutting sheath 336 is then advanced to sever and trap tissue bulging into indentation 334. The biopsy tool may then be removed from the tissue, with sample tissue still trapped in indentation 334. Antenna 331 physically helps to stabilize the tissue and to guide trocar 334 to the correct site. This helps ensure that tissue collected in indentation 334 is from the same region that was optically sampled by antenna 331. Similarly, nibbling probe 341 (FIG. 3E) removes tissue using tissue morselator 355 with washing and suction channel 356 surrounding morselator 355. If tissue is identified as containing contrast, the tissue is removed in small morselated pieces. In this way, the margins of resection may be made clear of disease, while sparing the normal tissue as much as is safe. This may allow for minimally invasive surgical procedures based upon optical contrast guidance. For example, a breast probe may be used to nibble out a breast tumor through a small hole, turning an invasive procedure into a minimally invasive lumpectomy. Alternatively, morselator 355 can be replaced with other tissue removing mechanisms, such as ablation fibers, tissue homogenizers, or other approaches. Surface scanning may also include bands, disks, or patches that are used externally, such as band 352, attached to head 362 (FIG. 3F).

As noted above, a probe can be noninvasive or invasive. First, a probe may be constructed to image from the surface of the tissue, rather than penetrating the surface of the tissue. For example, emitter fibers 131A to 131N and detector fibers 151A to 151M may be woven into surface probe 303, or assembled into headband 352 and wrapped around a tissue, such as head 362 (FIG. 2F). From such a surface probe, an image can be reconstructed using imaging algorithms that are known. This image can then be further processed by localization of contrast agent 141, using the present method. Alternatively, a probe can be automated to invasively sample at different depths as it is pushed into the tissue. This simplified probe requires only one emitter and one detector, and depth can be estimated by the fractional time passing between entry and full insertion, with the speed of the probe assumed to be constant during insertion and sampling. Alternatively, the probe can be motorized and move into the tissue in defined amounts, such that the depth of the probe at each sample is precisely known and under device control.

Of note, when needle 133A/133B penetrates into tissue 135, the photons traveling between the emitting and collection ports of needle 133A/133B take a wide range of paths, as shown in FIG. 2 as paths 283A through 283F. This scattering is in contrast to other surface imaging methods that shine light at a tissue surface and detect the reflectance of light as it scatters back from the surface. This scattering process was shown in FIG. 2, with the needle placed into reference 203. Some photons may take relatively direct paths, such as paths 283A and 283B, while others take longer paths that stray far from the direct visual line between emission at site 291 and collection at site 293, such as paths 283C and 283D. The changes in direction for photon paths 283A through 283D could represent scattering, or nonelastic events such as fluorescence or wavelength shifts. Still, other photons stray along lines that result in absorbance, such as path 283E, or escape from the tissue, such as path 283F, and never can be collected. This range of paths is due to the scattering of light by tissue, in which an emitted ray of photons turns into a diffuse glow as the original directionality of the photon beam is lost, which destroys standard optical imaging clarity, similar to photons becoming randomized in a fog leading to the images of far-away objects becoming obscured. The present device takes advantage of this effect as the scattering provides an averaging and volume sampling function. When detected illumination is measured after it has propagated through the tissue over substantially non-parallel multiple courses taken through the tissue between the time the photons are emitted and then detected, many regions of the tissue can be sampled, not merely the tissue on a narrow line between emission and detection. This allows a small but important feature, such as a small tumor, to be detected even if it happens outside of the line directly between the emitter and detector.

EXAMPLES

The breadth of uses of the present invention are best understood by example, three of which are provided below. These examples are by no means intended to be inclusive of all uses and applications of the apparatus, merely to serve as case studies by which a person, skilled in the art, can better appreciate the methods of utilizing, and the scope of, such a device.

Example 1

Targeting of a Needle in a Human Tissue to a Contrast-Positive Site

Localization of a tissue at which biopsy should be collected may be assisted using a contrast that collects at the target site. Such a device would be useful for prostate cancer. One in five men will develop the disease, which exceeds even the incidence of breast cancer in women. The standard method of diagnosis, prostate biopsy, has a 20% chance of missing a cancer that is present. Thus, repeat biopsy tests are frequently required. Currently, less that 20% of all prostate tumors can be felt during examination, and as prostate cancer is not well seen by current imaging methods, prostate biopsies are in effect performed blindly.

Many methods of targeting a contrast agent to prostate cancer can be utilized. For example, as discussed earlier, it is known that certain cell types possess surface markers such that cancer cells may have surface receptors that their neighbor cells do not. This allows for contrast agents to be targeted to specific sites. Targeting may also be less specific, such as in the use of photosensitizing agents (e.g., ALA) that preferentially accumulate within cancerous tissues through conversion to fluorescent porphyrin intermediates.

Data from an actual experiment are presented. Excised human prostate is used as a sample tissue. In this example, a contrast has been injected into a tissue model to simulate localization using such techniques, and is achievable using known targeting methods. A small amount (100 $\mu$L) of a blue dye, a mixture of FD&C Reds #40 and Blue #1 (Shilling, Hunt Valley, Md.), was used as a contrast agent. While an excised prostate differs optically from live human tissue, the presence of a contrast agent in the excised tissue provides a similar level of added contrast as would be expected using a contrast agent in vivo; similarly, while this dye is not expected to serve as a contrast agent of choice in vivo, the signal from this dye can be processed in a manner analogous to the targeted contrast dyes that would be used under such circumstances. Therefore, success in this model indicates feasibility and workability in live tissue.

Spectral data are collected as the needle is advanced, in this system between 5 and 20 spectra are collected per second. Thus, during the advance of a needle using the described system, between 50 and 1000 spectra are typically collected during an entire procedure. Each spectrum is collected at a different place, as the needle is slowly advanced. The spatial separation between each neighboring spectrum is typically under 1 mm. That is, between the time a spectrum is collected and the next spectrum is collected, the needle moves less than 1 mm. Four spectra out of the nearly 500 spectra collected during a study on human prostate were selected to be shown in FIG. 4. When the needle was about to enter the prostate, spectrum 522 was collected as the needle was touching of the capsule of the prostate. Next, spectrum 525 is seen after passage into the interior of the capsule. Spectra 522 and 525 are distinctly different, and a the different tissue layers of the prostate can be identified from such spectra based upon separation algorithms known in the art. Next, upon placement of the needle at a site containing contrast, spectrum 529 is seen. The spectral feature of the contrast can clearly be seen, even by eye, and is greatest at 631 nm, shown as peak 532. Later still, as the needle is withdrawn, the blood accumulating behind the needle as it is pulled back can be seen in spectrum 535 as blood feature 538.

Figure 4:
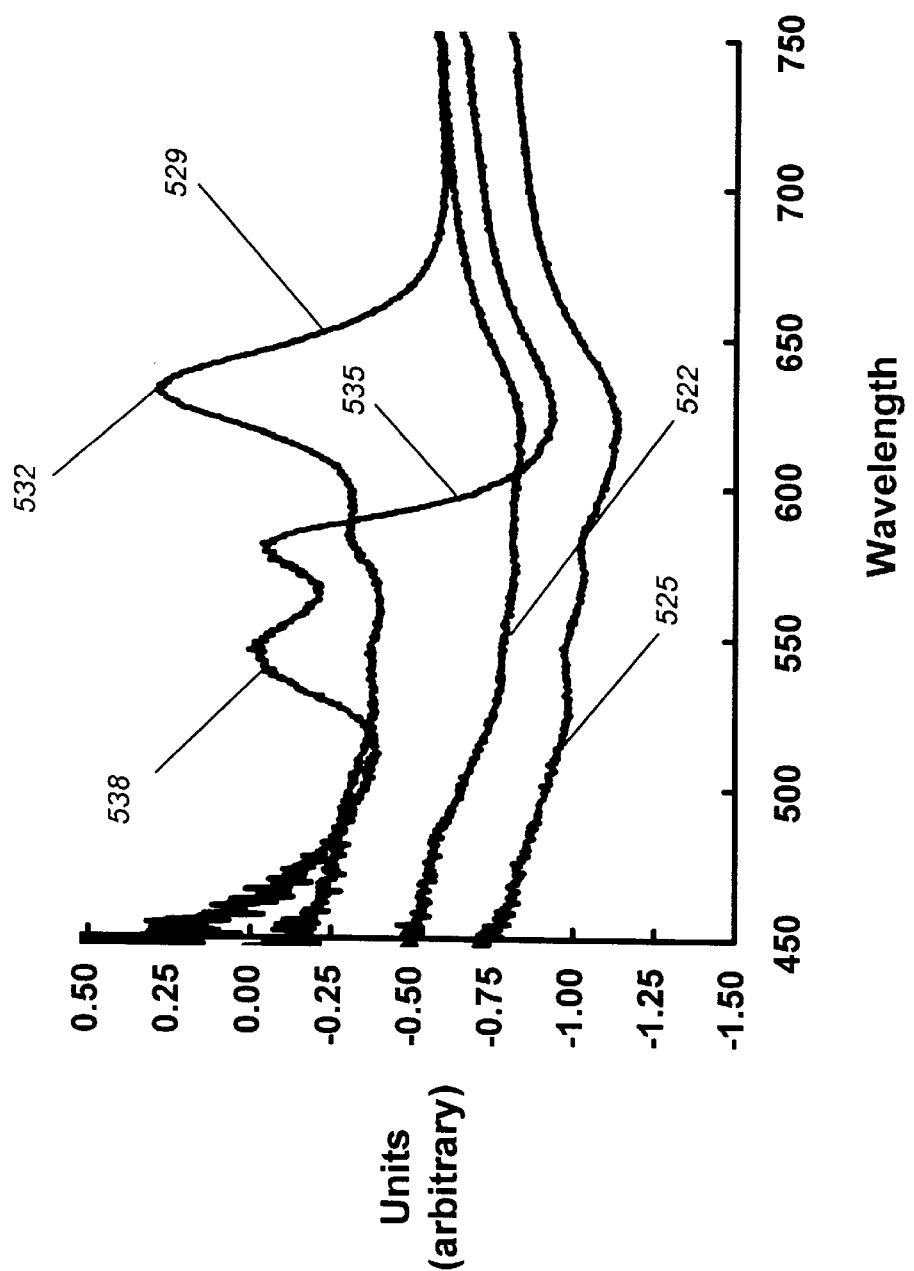
FIG. 4 shows four optical spectra collected as a needle was inserted into human prostate containing contrast using an instrument constructed in accordance with the present invention.
Figure 5:
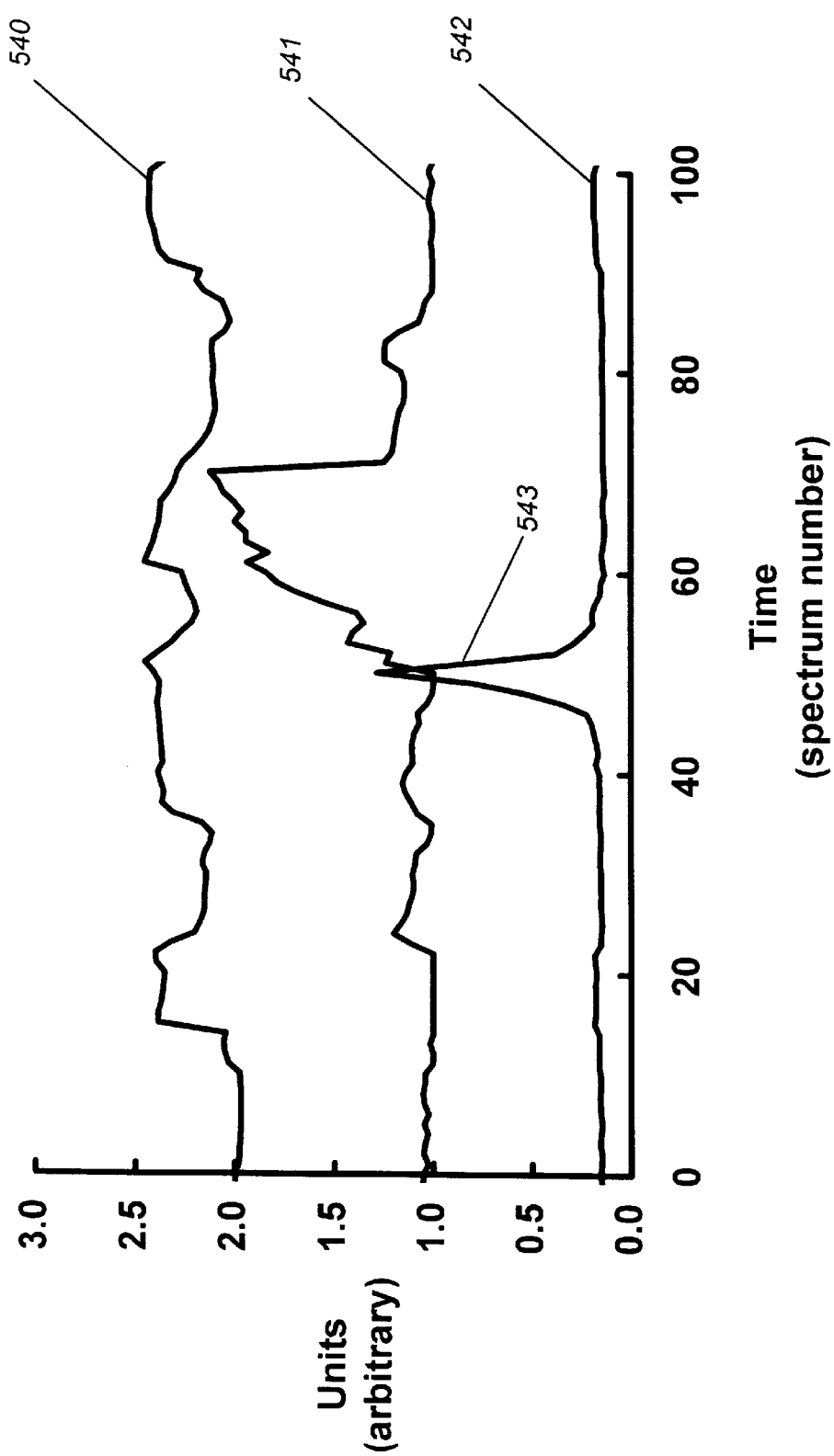
FIG. 5 shows a graph generated by analysis of data collected from human prostate.
Figure 6:
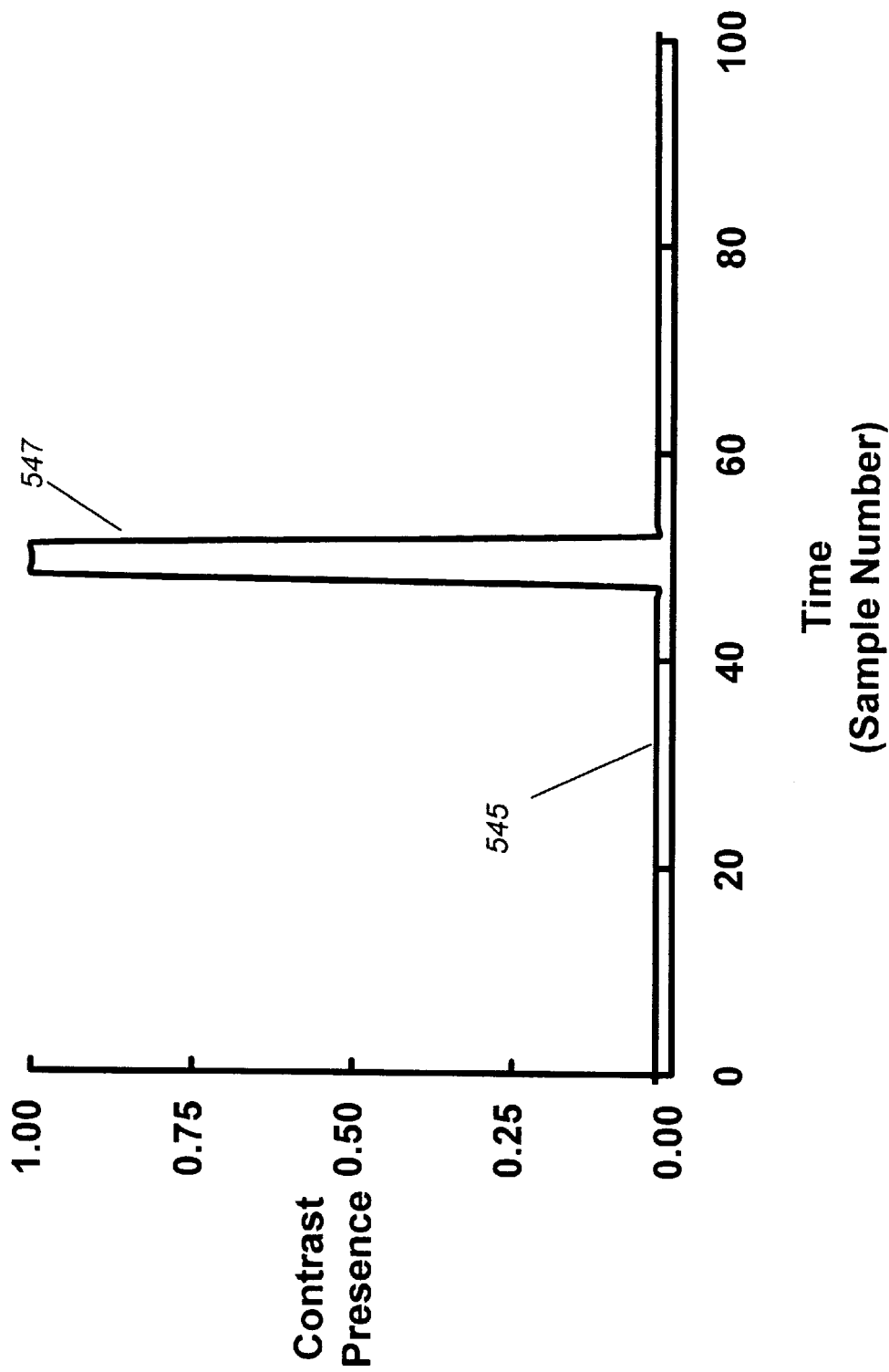
FIG. 6 shows optical spectra processed for the presence or absence of contrast using a threshold, clearly indicating the location of contrast within the prostate.

While FIG. 4 showed portions of individual spectra at four points in time, the data is in reality being processed in real time, and hundreds of spectra are collected. The results of analyzing these hundreds of spectra, and plotting the analyzed results over time as the needle is advanced, are shown in FIG. 5. Here, the raw spectra are not shown. Rather, each spectrum has been analyzed and the results of this analysis are displayed as a point on three curves: light scattering 540, hemoglobin concentration 541, and contrast signal strength 542. Note that scattering 540 and hemoglobin 541 have features that vary with time, but identification of the location of the tumor may not be obvious upon inspection of these results. In comparison, contrast signal 542 peaks at sample numbers 48 to 51, shown as peak 543, and clearly shows the localized collection of contrast agent. Peak 543 is sufficiently strong that it can clearly be seen, even by eye, and represents the point at which a tumor biopsy should be collected. Plotting contrast signal 542 on a graph on a monitor for a physician to use in real time would serve as a visual indication to the physician that a biopsy should be collected at a particular place. Alternatively, this analysis could be more processed. For example, in FIG. 6, contrast presence curve 545 is calculated using a predetermined contrast signal threshold, and displayed as a graph over time. The physician is encouraged to collect a biopsy when the signal is strong, such as at peak 547. In related experiments, the tissue in such studies has been cut open when a peak similar to peak 547 is seen, and the needle has been found to be accurately located at the site of contrast, confirming the feasibility and accuracy of this technique. Thus, the present system and method has allowed for targeted delivery of an instrument to the stained region. Further, had the invasive instrument been an interventional tool, a target intervention, such as biopsy or therapy, could have been performed at the target site.

The information from this detection and localization can be presented in a number of ways, including a word indicating the presence or absence of a specific tissue type, a table (such as the percentage of signal arising for one or more contrast agents), an identification of the contrast-stained tissue by depth, a graph (such as the presence or absence of a tissue type over time, as shown above, or a distance to a target site), a number (such as the distance to an object), an image (such as the location of the target tissue), a localization (such as a measurement of angle and distance of the target tissue), or a displayed word that changes according to the location and concentration of the contrast agent. Different curves could be displayed, and no undue limitation is intended by the selection of the curves shown FIGS. 4, 5, and 6.

The contrast agent used in this example could have been a fluorescent probe, which would have suppressed the background signal and greatly enhanced the specificity of the detection at low concentrations of marker. Similarly, a contrast agent that "turns on" upon binding or internalization into prostate cancer would give an even greater enhanced contrast. Any optical contrast agent or reporter could be used here, provided that the optical light source and light detector are configured to detect the signal. Configuration of the source and detector include the ability to detect fluorescence, time- or frequency-resolved data, and the like.

Such measures can be used for guidance, which can be as simple as moving the needle in a manner so as to increase the concentration of contrast until a maximum is reached. The optical probe can be constructed using more than two fibers, so as to provide a difference signal of different fiber sets, for example spaced to the left, center, right, superior, and inferior sides of the needle. A directional output signal may be as simple as:

If the left side shows a higher contrast signal, then the tumor is off to the left, If the right side shows a higher contrast signal, then the tumor is off to the right, If the superior side shows a higher contrast signal, then the tumor is superior to the probe, If the interior side shows a higher contrast signal, then the tumor is inferior to the probe, and, If the center is stronger than the left, right, superior, and inferior signals, then the needle is heading toward the tumor.

This algorithm can also be refined to take into account the relative differences of the left, right, superior, and inferior signals, to produce an angular estimate of distance.

Similarly, such measures can be used merely for detection, such as the presence or absence of prostate cancer. Note how clear the presence of contrast is in FIGS. 4 and 7. This suggests that an entire organ, such as the prostate, could be scanned using a detection probe. For example, if a rectal probe was placed in the rectum and near the prostate, and after administration and localization of a contrast agent, then cancer can be detected if the spectrum of the contrast agent is seen during transillumination of the prostate, if no spectrum is seen then cancer is absent. Such a detection study can be followed up using a contrast guided biopsy needle for diagnosis, a contrast guided nibbling tool for cancer removal, or using a contrast-sensitive imaging system to image the distribution and tumor load within the prostate. In current prostate biopsy, an ultrasound probe is inserted to guide the biopsy needle. Optical fibers may be added to the ultrasound probe or biopsy needle, such that an image of the target tissue, as determined from the location and distribution of a targeted contrast, may be overlayed on the ultrasound image. This would result in an ultrasound image with areas suspicious for cancer highlighted on the image.

Other types of output may be considered, but fall within the scope of this invention if the signal is a contrast-based guidance signal that represents a function of information related to the presence, location, or distribution of tissues, or is used to guide a probe or device into a position in the body based upon a signal from an endogenous contrast. Various forms of probes may be considered, including needles, trocars, catheters, radio-frequency antennae, cryosurgery probes, laser surgery beams, endoscopes, video cameras and fibers, and the like.

The analysis in this example uses the entire collected spectrum in order to extract a measure of localization or distribution of the contrast agent or target tissue. The tools for performing this extraction from measured spectra are well known, and include, but are not limited to, partial least squares (PLS), principal components analysis (PCA), SIMCA, genetic algorithms, and fuzzy set theory. On the other hand, the contrast guidance algorithm could be deceptively simply. For example, if the amount of light returning to the detector at one wavelength, say at a contrast peak of 631 nm, decreases as the needle approaches the blood vessel, then the needle could use a signal surface mount LED and a solid state photodiode detector, and the algorithm could be as simple as:

a) the proximity of the needle to the tumor is inversely proportional to the intensity of the returning light; and, b) when the intensity of the measured light is below a certain threshold then the needle is in a tumor.

A more complex, but still simple, algorithm could use difference of absorbance at two wavelengths, for example at 631 nm and 660 nm, where the difference of $A_{631}$ and $A_{660}$ corrects for baseline absorbance and allows the contrast concentration to more reliably extracted. This latter method requires only two wavelengths, allowing for simple light sources such as two wavelengths of surface-mounted LEDs, rather than a broad spectrum source, and a simple light detector, rather than a more complex spectrophotometer. Again, the act of guidance is performed by a means for generating a targeting signal.

Note that the system operates in real-time using information regarding the tissue collected from the tip of the instrument. This overcomes all of the four limitations of conventional guidance approaches listed at the start of the background section: blindness of approach, lack of inherent contrast, real-time registration of the information with what is actually at the tip of the needle, and portability and affordability.

Example 2

Surface Detection and Imaging of Isosulfan-Positive Areas

Another example of a targeted procedure is biopsy of lymph nodes for breast cancer. Breast cancer is the most common cancer in women worldwide, second only to cervical cancer, and is a leading cause of death in women.

The treatment of breast cancer requires determination of the grade and spread of the tumor, a process called staging. Determination of spread to the lymph nodes is a key to proper treatment selection and increased survival. When breast cancer is diagnosed, the sentinel lymph node is identified and biopsied. Sentinel nodes are the main lymph node draining the tumor. They are currently identified by injection of a radioactive substance, which is traced using a Geiger counter (e.g., U.S. Pat. No. 5,846,513 discussed under Background) with or without the injection of blue contrast. Sentinel breast nodes can be marked by injection of the tumor with blue contrast, as the contrast migrates to the sentinel lymph node or nodes, staining them blue. This blue dye is approved for use in humans and is easy to spot once the node has been found, but is difficult to find without making an incision.

The blue contrast used in this example is isosulfan blue (Lymphazurin™, U.S. Surgical Corporation, Norwalk Conn.). Lymphazurin is a sterile, aqueous solution FDA approved for subcutaneous administration for use in delineating lymphatic vessels, including tracking lymph nodes involved in cancer.

Figure 7:
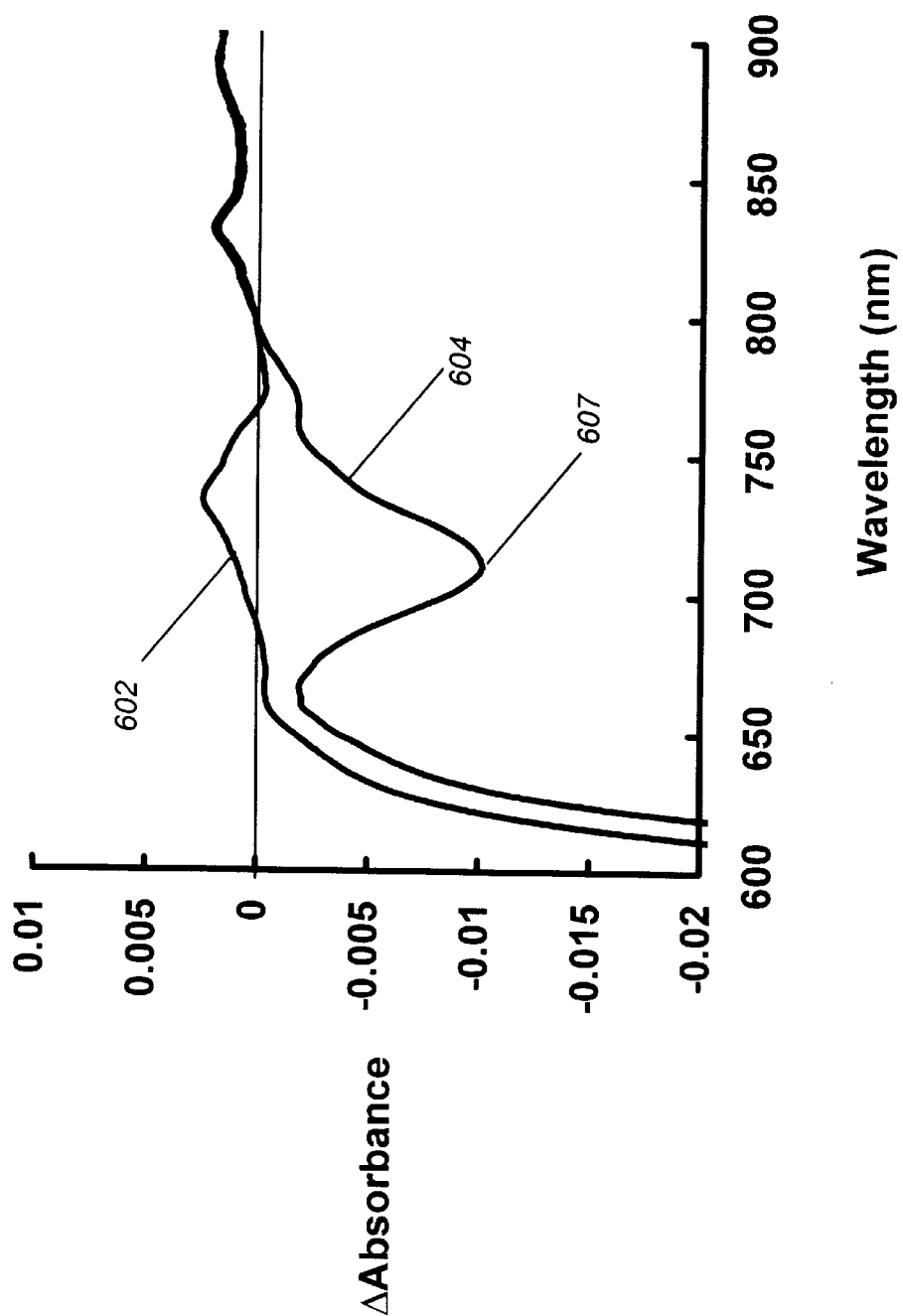
FIG. 7 shows two first differential optical spectra collected from live human tissue, with and without the FDA approved contrast isosulfan blue.

In experimental tests, we demonstrated that isosulfan blue containing regions of tissue can be externally localized and targeted using optical means. In the laboratory, we first demonstrated that isosulfan blue contrast can be detected in mixtures of hemoglobin and contrast agent. As the primary absorber in the body between 550 and 900 nm is hemoglobin, we measured mixtures of hemoglobin and Isosulfan, and found unique features that allow differentiation of isosulfan blue from hemoglobin. Using these unique features, the signature of isosulfan blue could be extracted from hemoglobin mixtures using the slope or value of the first differential signal near 697 nm (FIG. 7). Spectrum 602 from live human tissue without a buried isosulfan target can be compared to spectrum 604 from live tissue with an isosulfan target. Spectrum trough 607 is unique to the presence of isosulfan in the body. A great advantage of this feature is that light above wavelengths of 650 nm travel deeply into the body, allowing trough 607 to be detected at depths of up to 10 cm. Other contrast agents with features well into the infrared are known. Contrast agents with spectral features occurring between 800 nm and 2 microns are be particularly useful, as there are virtually no significant first differential spectral features in human tissue at those wavelengths, save for several absorbance peaks and troughs caused by water.

Figure 8:
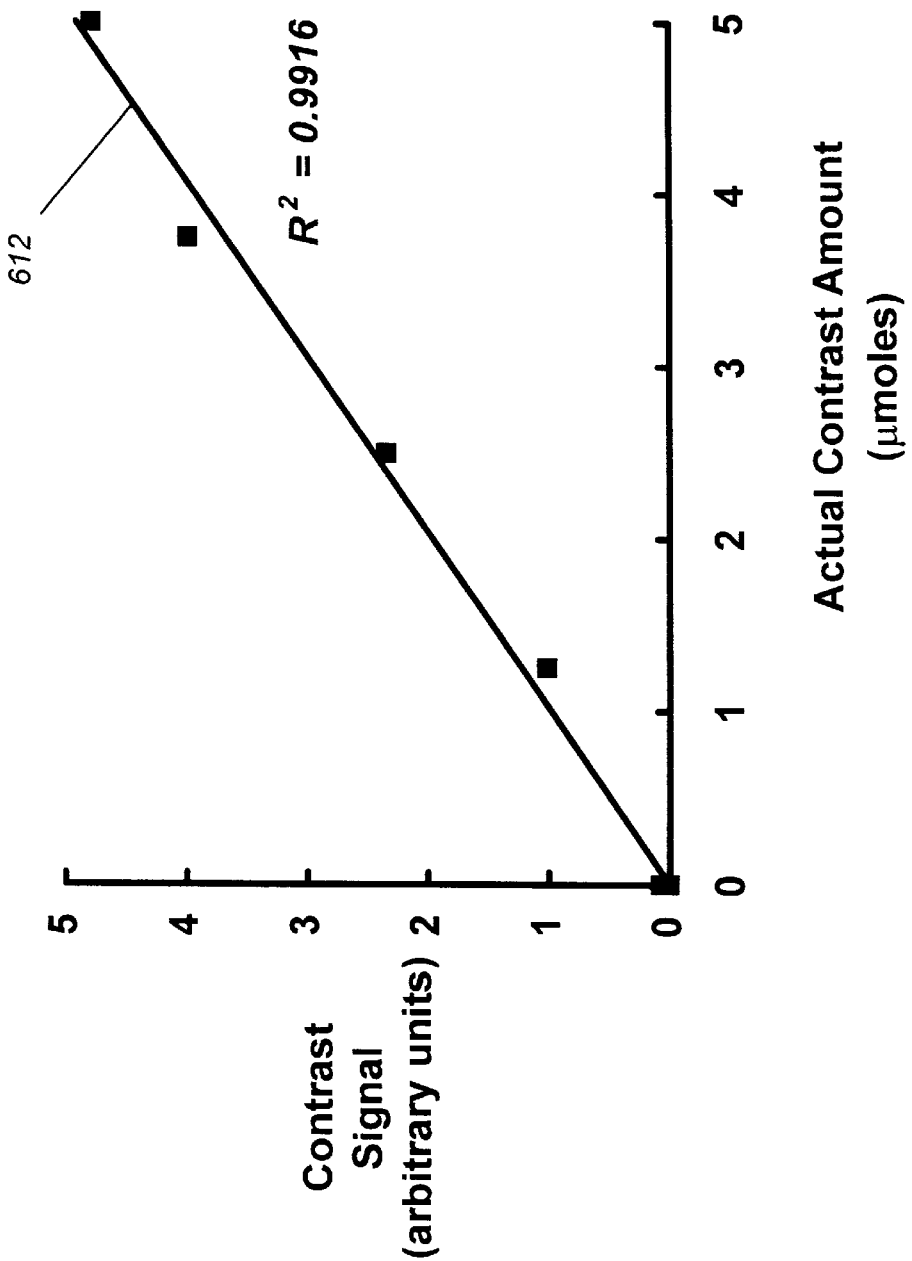
FIG. 8 shows a graph of the linear response of contrast signal as the amount of contrast within a living tissue is increased.

Next, in living human tissue we demonstrated that, as the amount of contrast in a sample tissue was increased, in vivo contrast signal 612 linearly increased, as shown as FIG. 8. The high sensitivity in FIGS. 7 and 8 becomes clear when it is noted that the volume of isosulfan blue in these studies ranged between 12 and 60 µL (between 250 nanomoles to just over 1 micromole of isosulfan blue) located several centimeters under the skin surface. As isosulfan blue is preferentially passed through the lymphatic system, this agent can serve as a source of differential contrast in vivo; namely that tissues which take up the contrast agent will appear distinct from those tissues that do not take up the contrast in similar amounts. Such differential contrast can also be achieved by having the contrast agent bioactivated at the target site, and "turn on" or "turn of" only in desired tissues.

Last, we used this first differential signal approach to generate an external image of the contrast-positive lymph nodes in a tissue model, as shown in FIG. 9A. The scanning probe made for this study used multiple fibers for emission and detection, and serves as a model for an instrument that can be scanned within a wound or on the skin. An isosulfan blue target was created by placing isosulfan on filter paper.

A piece of filter paper measuring 2 mm×3 mm, and contained 0.20 µL of contrast (4 nanomoles of isosulfan blue) was placed 2 cm below the scanning surface in vivo. Data were collected by scanning the detection fibers across the area to be monitored. A 30×30 mm area was scanned, and 10 spectra were collected for each scan pixel. In this case, the fiber was singular, though a 1-D linear array, or a 2-D array, would have worked equally well or better. Data from the above experiment were collected in 2-D by scanning the surface probe over the tissue to collect a grid of data. Image 633 clearly shows the location of the isosulfan blue target as contrast signal peak 635. An overhead view of FIG. 9A is shown in FIG. 9B, where it can be seen in image 637 that well-circumscribed area 639 indicates the location and distribution of the isosulfan blue, as well as of the target tissue. Therefore mapping of the positive sentinel nodes in tissue is achievable.

This experiment demonstrates that optical contrast can be used to produce a signal that varies with localization and distribution. As shown previously in Example 1, this can be used for targeting as the signal increases as the sensor is moved closer to the contrast source.

This experiment also confirms that such a system and method can work to form images in vivo using a medical instrument, used externally or internally, to measure light that has traveled through opaque tissues. Such scanned fibers can be replaced with a probe containing a CCD detector and surface mounted LEDs to allow rapid and simultaneous imaging of multiple pixels. Such a system would allow reconstruction of contrast maps, as well as guidance toward contrast positive nodes in humans using an optically-enabled invasive instrument.

Alternatively, a fluorescent contrast could be substituted, and the fluorescence imaged in a similar manner.

Example 3

Multicolor Contrast Labeling

Dual or multiple contrast labeling is a technique frequently used in cytology and other ex vivo laboratory disciplines. In this technique, different contrast agents are added to the same sample, in order to extract additional information. This approach can also be applied in vivo using the present method.

For example, many tissues may take up a first contrast agent, as these tissues have a receptor for the first contrast agent. In addition, a different combination of tissues may take up a second contrast agent, as these different tissues have a receptor for the second marker. A cancer may be identified as having both receptors, or the presence of one without the presence of the second. In either case, the ability to detect, localize, image, and target using two or more contrast agents simultaneously may be important.

Figure 10:
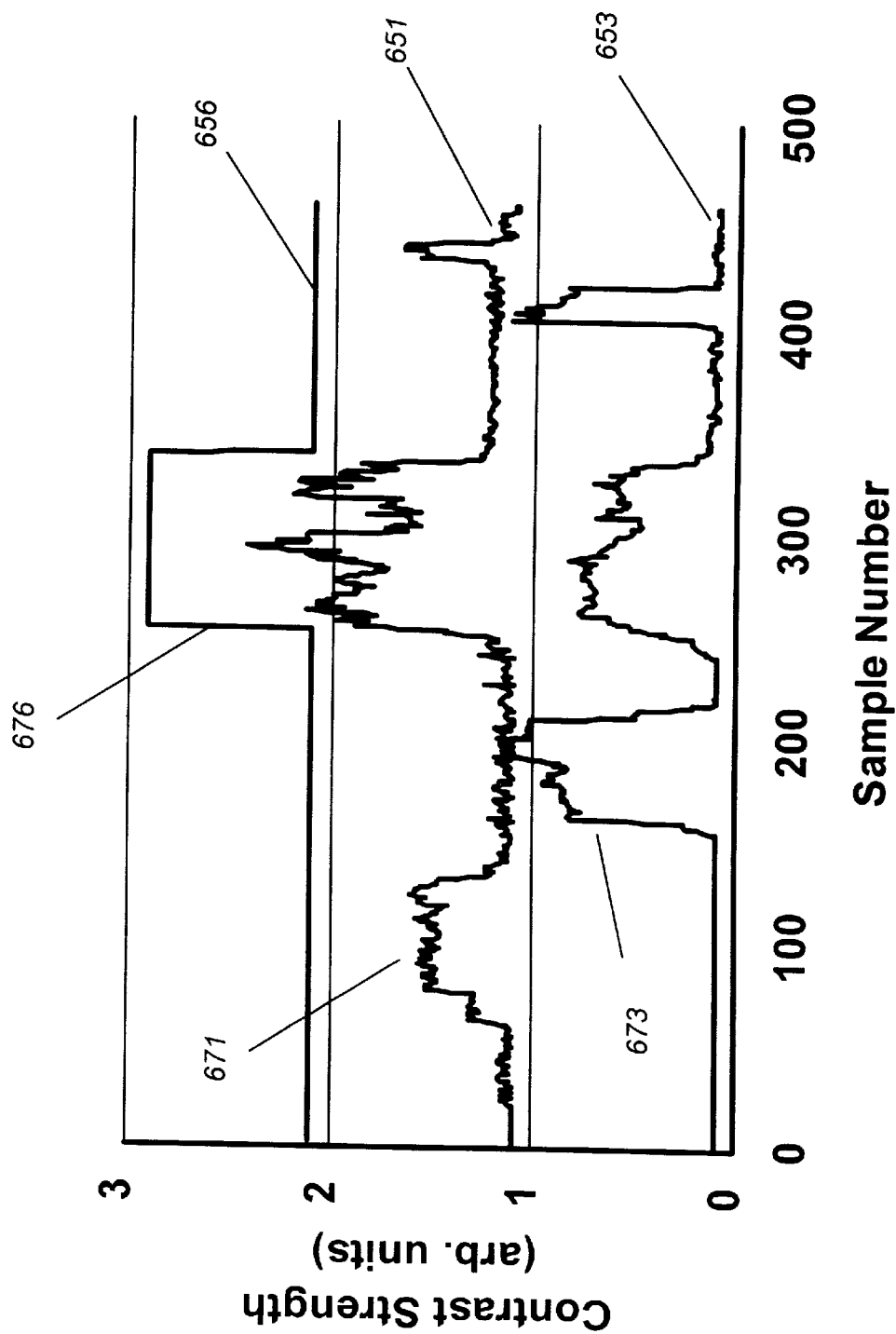
FIG. 10 shows a two contrast study in which two contrast agents were tracked in a tissue model.

As a test of this, the probe was used to differentiate regions containing no exogenous contrast agent from regions containing the a red contrast (FD&C Reds 40 and 3, Schilling, Hunt Valley, Md.) or the isosulfan blue contrast used in Example 2, as well as from regions containing both the red and blue contrast agents. A tissue model was created using thickened, homogenized beef. Volumes of contrast (3 µL isosulfan blue and 14 µL red contrast per cc tissue homogenate) were mixed into selected regions of this model into this model, creating regions with the no contrast, the first contrast alone, the second contrast alone, and both contrast agents. The raw data (not shown) were processed in a similar manner to that shown in Examples 1 and 2. The calculated contrast signal strength for each contrast agent is plotted in FIG. 10. Red contrast strength curve 651 was calculated using a differential absorbance feature at 556 nm, while blue contrast strength curve 653 was calculated as shown in Example 2. Coincidence curve 656 indicates when both contrast agents are present using a threshold value. In FIG. 10, a region containing red dye can be seen as peak 671 for sample numbers 62 to 133, a region containing blue contrast alone can be seen as peak 673 for sample numbers 159 through 218, while a region containing both red and blue contrast can be seen from coincidence peak 676 for sample numbers 251 through 335. The region with both the first and second contrast agent is clearly detectable. Three or more contrast agents can be analyzed using similar methods.

This data can be presented in as a graph, as shown in FIG. 10, or the raw data can be listed in table form, as shown below:

TABLE

A numeric table of some of the data shown graphically in FIG. 10

| Sample No.: | 0 | ... | 96 | ... | 168 | ... | 268 | ... | 348 |
|---|---|---|---|---|---|---|---|---|---|
| Contrast A: | 0.0 | ... | 1.2 | ... | 0.1 | ... | 0.8 | ... | 0.3 |
| Contrast B: | 0.0 | ... | 0.0 | ... | 1.3 | ... | 1.1 | ... | 0.1 |
| Both A and B: | No | ... | No | ... | No | ... | Yes | ... | No |

We have discovered an improved method and device that measures tissue and allows the detection, localization, imaging, and targeting of contrast-enhanced tissues within the human body using optical elements coupled to medical instruments, either externally or invasively, or both, using light emitted and detected from the body. A system constructed in accordance with the invention has been built and the method tested in several configurations in models, animals, and humans, and these have immediate application to several important problems, both medical and industrial, and thus constitutes an important advance in the art.

What is claimed is:

1. A method of externally or internally measuring a target site within a living subject, comprising:
   (a) administering to the subject an optical contrast agent selected so as to provide measurable contrast for said target site in vivo;
   (b) waiting until said contrast agent has achieved sufficient distribution and localization within the body;
   (c) providing a medical device or instrument optically coupled to a light source, a light detector, or both, and using said device or instrument during a medical or surgical procedure upon the subject;
   (d) illuminating the subject with light from the light source, said light source selected such that the contrast agent in vivo may interact with and modify the illuminating light;
   (e) detecting modified illuminating light after passage through an opaque region of the body using the light detector;
   (f) determining a measurable parameter of the target site using the detected light based upon a function of the distribution and localization of said contrast agent; and,
   (g) generating an output signal in response to said determination.

2. The method of claim 1 wherein the optical contrast agent is selected from the group of contrast agents consisting of isosulfan blue or other absorbing contrast agents, indocyanine green, porphyrins, or other fluorophores, methyl red or other biologically responsive dyes, colored or fluorescent proteins and other gene products, quantum dots and other spectroscopically distinct physical constructs, contrast-filled micelles, or other optical contrast agents.

3. The method of claim 1 wherein the step of administering the contrast agent includes the step of injection, ingestion, viral delivery, or synthesis within the subject using genetic mechanisms or encapsulated biofactories.

4. The method of claim 1 wherein the step of administering the contrast agent includes the step of administering multiple optical contrast agents, each targeted to a different receptor, and wherein the step of determination is based upon a function of the distribution and localization of said multiple contrast agents.

5. The method of claim 1, wherein said contrast agent further requires an activation, inactivation, or synthesis step in vivo.

6. The method of claim 5, wherein said contrast agent is selected from the list of activatable agents consisting of cleavable indocyanine dye, acid-cleavable transferrin bound dyes, and other activatable contrast agents.

7. The method of claim 1, wherein the optical contrast is coupled to a targeting moiety.

8. The method of claim 7, wherein the targeting moiety is selected from the list of targeting moieties consisting of antibodies, antibody fragment, receptor binding site or substance, and translocator binding site or substance.

9. The method of claim 1, wherein said medical instrument is a scanning optical probe, said contrast agent is isosulfan blue, said administration consists of injection into the margin of a tumor, and said output signal is detection of the presence and location of contrast-absorbing sentinel lymph nodes.

10. The method of claim 1, wherein said medical instrument is a modified rectal ultrasound probe, said contrast agent is targeted to a prostate-specific receptor, said administration consists of oral ingestion, and said output signal is an ultrasound image overlaid with the presence and location of prostate cancer.

11. The method of claim 1, wherein one or more of steps (a) through (g) are repeated at one or more points in time, wherein said repeating is effective to track the said distribution and localization of said agent over time.

12. The method of claim 1, further including the step of comparison to a reference signal.

13. The method of claim 1, further including the step of comparison to a baseline signal in the absence of contrast.

14. The method of claim 1, wherein said measurable parameter is a function of the local environment of said contrast agent.

15. A system for externally or internally measuring a target tissue within an opaque portion of the body of a living subject, comprising:
   (a) an optical contrast agent for providing a source of contrast, said agent selected so as to provide a differential contrast between said target tissue and other tissues, and said agent administered to the subject so as to have achieved distribution and localization within the body;
   (b) a light source for illuminating a portion of said subject with illuminating radiation, said distributed contrast agent at least potentially disposed to interact with and modify said illuminating radiation;
   (c) a light collector for collecting a portion of said radiation, said collected portion having passed through an opaque region of the body of the subject, and for providing a detected signal in response to said collected portion;
   (d) a medical instrument for use on or within said subject during a medical procedure, said medical instrument coupled to said light emitter, said light collector, or both; and,
   (e) means for determining a measurable parameter of said target tissue based upon said detected signal, said measure based upon a measurement function of said distribution and localization of said contrast agent, and for generating an output signal in response to said determination.

16. The system of claim 15, wherein said light source is further comprised of multiple light sources.

17. The system of claim 15, wherein said illuminating radiation has at least one wavelength between 200 nm and 2 $\mu$m.

18. The system of claim 15, wherein said light collector is further comprised of multiple light detector elements.

19. The system of claim 18, wherein said multiple detector elements comprise a CCD array.

20. The system of claim 15, wherein said measurable parameter is a detection of the presence or absence of said target tissue in the body.

21. The system of claim 15, wherein said measurable parameter is a localization of said target tissue within the body in at least one dimension.

22. The system of claim 15, wherein said measurable parameter is a direction of said target tissue.

23. The system of claim 15, wherein said measurable parameter is a distance to said target tissue.

24. The system of claim 15, wherein said output signal is an image of the distribution of said target tissue within the body.

25. The system of claim 15, wherein said measurement function is based upon an optical feature selected from the group of features consisting of absorbance, fluorescence, Raman shift, excitation-emission maps, optical rotation, fluorescence decay, phase shift, time delay, or other optical features related to the interaction of said contrast agent with said illuminating radiation.

26. A method for targeting an invasive medical device or instrument toward a target location in a living subject, comprising:

(a) administering an optical contrast agent to the subject;

(b) waiting until the contrast agent has achieved adequate distribution and localization within the body;

(c) providing a medical instrument that is optically coupled to a light source, a light detector, or both, and using said instrument during an invasive medical or surgical procedure upon the subject;

(d) illuminating the subject with light from said light source;

(e) detecting modified light with said light detector after passage of the source light through an opaque region of the body and after possible interaction and modification of the source light by the contrast agent;

(f) determining the present location of the medical device or instrument with respect to said target location based upon the modified, detected light; and, (g) generating an output signal in response to said determination.

27. A system for targeting an invasive medical device or instrument toward a target location in a living subject, comprising:

(a) a contrast agent, said contrast agent administered to the subject so as to have achieved distribution and localization within the subject;

(b) a light emitter for illuminating a portion of the subject with illuminating radiation, said emitter optically coupled to the subject, and said administered contrast agent potentially disposed to interact with and modify said illuminating radiation;

(c) a light collector for collecting a portion of the illuminating radiation, said collected portion having passed through an opaque region of the body and said collector optically coupled to the body, and for providing a detected signal in response to said collected portion;

(d) a medical instrument for use within said subject during an invasive procedure, said medical instrument coupled to said light emitter, said light collector, or both;

(e) means for determining a positional estimate of the present location of said medical device or instrument with respect to a target location based upon said detected signal, said measure based upon a measurement function of said distribution and localization of said contrast agent in relation to a position of said medical device, and for producing an output signal in response to said determination.

28. The system of claim 27, wherein the optical coupling of the emitter, the collector, or both emitter and collector, to the subject is achieved by tissue penetration.

29. The system of claim 27, wherein said positional estimate is a finction of the accuracy of placement of the probe at said target location.

30. The system of claim 29, wherein said function of the accuracy of placement is a true or false indication as to whether or not the probe is accurately placed.

31. The system of claim 27, wherein said positional estimate is a direction of a target tissue.

32. The system of claim 27, wherein said positional estimate is a distance to a target tissue.

33. The system of claim 27, wherein said positional estimate is a localization of the device with respect to tissue type.

34. A method for targeting a prostate biopsy needle toward potential prostate cancer sites in a patient, comprising:

(a) administering to the patient an optical contrast agent targeted to cancer-specific prostate cell surface antigens;

(b) waiting until the contrast agent has achieved adequate distribution and localization within the body;

(c) providing a biopsy needle that is optically coupled to a light source, a light detector, or both, and inserting the needle into the patient's prostate;

(d) illuminating the subject with light from said light source;

(e) detecting modified light with said light detector after passage of the source light through an opaque region of the body and after possible interaction and modification of the source light by the contrast agent;

(f) determining the present location of the biopsy needle with respect to the prostate cancer, based upon the modified, detected light; and, (g) positioning the biopsy needle at an identified potential cancer site and collecting a biopsy sample at that site;

(h) repeating steps (d) through (g) until a sufficient number of prostate biopsy samples have been collected.

35. A method for removing a breast tumor using a minimally invasive medical probe, comprising:

(a) intravenously administering an optical contrast agent to the subject;

(b) waiting until the contrast agent has achieved adequate distribution and localization within the body;

(c) providing a minimally invasive tissue removal device that is optically coupled to a light source, a light detector, or both, and using the device or instrument during an minimally invasive lumpectomy procedure upon the subject;

(d) illuminating the subject with light from the light source such that the contrast agent in vivo may interact with and modify the illuminating light;

(e) detecting modified light with the light detector after passage of source light through an opaque region of the body and possible interaction and modification of the source light by the contrast agent;

(f) determining a positional estimate of the present location of the medical device or instrument with respect to any remaining breast cancer based upon said modified, detected light; and, (g) generating an output signal in response to said measurement;

(h) removing tissue identified as breast cancer; and, (i) repeating steps (d) through (h) until a diagnostic or therapeutic endpoint is reached.

36. A medical system for determining the location of one or more sentinel nodes in breast cancer during a lymph node biopsy, comprising:

(a) a contrast solution of isosulfan blue for providing a source of contrast between said sentinel node tissue and normal lymph tissues, said agent injected into the periphery of said breast cancer so as to have achieved distribution and localization within the lymph nodes;

(b) a white light source for illuminating a portion of said subject with illuminating radiation;

(c) a light collector for collecting a portion of said illuminating radiation, said collected portion having passed through an opaque region of the body of the subject potentially containing said contrast agent, and for providing a contrast influenced detected signal in response to said collected portion;

(d) a medical probe for use on or within said subject during said node biopsy, said medical probe coupled to said light emitter, said light collector, or both; and, (e) means for determining the location of said sentinel nodes, said determination based upon said detected signal, and for generating an output signal related to a distribution and localization of said sentinel nodes in response to said determination.

37. A medical system for determining the presence or absence of prostate cancer during a rectal diagnostic procedure, comprising:

(a) a fluorescent contrast agent targeted to cancer-specific surface antigens for providing a source of contrast between prostate cancer cells and normal prostate tissues, said agent ingested orally and systemically absorbed so as to have achieved distribution and localization within the prostate;

(b) a monochromatic intensity modulated light source for illuminating the prostate with illuminating radiation, said distributed contrast agent at least potentially disposed to fluoresce in response to said illuminating radiation;

(c) a multielement light collector for collecting a portion of said fluorescent radiation, said collected portion having passed through an opaque region of the prostate, and for providing a detected phase and intensity signal in response to said collected portion;

(d) a medical ultrasound probe for rectal use during said prostate examination, said medical ultrasound probe coupled to said light emitter, said light collector, or both; and, (e) means for determining the presence and location of prostate cancer based upon said detected signal, and for generating an output image related to a distribution and localization of said contrast agent in response to said determination.

* * * * *